United States Patent
Mann et al.

(10) Patent No.: US 9,128,168 B2
(45) Date of Patent: Sep. 8, 2015

(54) METHOD OF DETERMING EXCRETION OF SODIUM AND OTHER ANALYTES

(75) Inventors: Samuel J. Mann, New York, NY (US); Linda M. Gerber, Brooklyn, NY (US)

(73) Assignee: Cornell University, Ithaca, NY (US)

( * ) Notice: Subject to any disclaimer, the term of this patent is extended or adjusted under 35 U.S.C. 154(b) by 1227 days.

(21) Appl. No.: 12/334,154

(22) Filed: Dec. 12, 2008

(65) Prior Publication Data

US 2009/0157328 A1    Jun. 18, 2009

Related U.S. Application Data

(60) Provisional application No. 61/007,708, filed on Dec. 14, 2007, provisional application No. 61/007,707, filed on Dec. 14, 2007.

(51) Int. Cl.
| | | |
|---|---|---|
| *G01N 33/00* | (2006.01) | |
| *G06F 19/00* | (2011.01) | |
| *G01R 33/44* | (2006.01) | |
| *G01N 33/70* | (2006.01) | |
| *G01N 33/493* | (2006.01) | |

(52) U.S. Cl.
CPC ............... *G01R 33/44* (2013.01); *G01N 33/70* (2013.01); *G01N 33/493* (2013.01)

(58) Field of Classification Search
CPC ....... G01R 33/44; G01N 33/70; G01N 33/493
USPC ........... 702/19; 600/573; 436/88, 98, 124, 43, 436/86, 126, 514, 63, 169; 422/402, 69, 422/420, 400, 408, 422
See application file for complete search history.

(56) References Cited

U.S. PATENT DOCUMENTS

| | | | | |
|---|---|---|---|---|
| 4,159,193 A | * | 6/1979 | Gauntley et al. | ................. 436/86 |
| 4,211,532 A | | 7/1980 | Tobari et al. | |
| 4,444,193 A | | 4/1984 | Fogt et al. | |
| 4,650,768 A | | 3/1987 | Cahill et al. | |
| 4,744,952 A | | 5/1988 | Ogita | |
| 5,229,299 A | | 7/1993 | Terry | |
| 5,234,813 A | * | 8/1993 | McGeehan et al. | ............ 435/7.9 |
| 5,374,561 A | * | 12/1994 | Pugia | ............................. 436/98 |
| 5,435,970 A | | 7/1995 | Mamenta et al. | |
| 5,559,036 A | * | 9/1996 | Mienie et al. | ................... 436/63 |
| 5,610,073 A | * | 3/1997 | Chu et al. | ........................ 436/98 |
| 5,702,955 A | | 12/1997 | Pugia | |
| 5,710,372 A | | 1/1998 | Becket | |
| 5,733,787 A | * | 3/1998 | Messenger et al. | ............. 436/98 |
| 5,804,452 A | * | 9/1998 | Pronovost et al. | ............ 436/514 |
| 5,871,769 A | * | 2/1999 | Fleming et al. | ............... 424/423 |
| 5,932,226 A | * | 8/1999 | Ordman | ........................ 424/400 |
| 5,955,370 A | * | 9/1999 | Kell | ..................................... 436/2 |
| 6,001,656 A | * | 12/1999 | Cast et al. | ...................... 436/98 |
| 6,042,543 A | | 3/2000 | Warwick et al. | |
| 6,210,971 B1 | * | 4/2001 | Messenger et al. | ............. 436/98 |
| 6,306,660 B1 | * | 10/2001 | Messenger et al. | ............. 436/88 |
| 6,413,473 B1 | * | 7/2002 | Bacon | ........................... 422/408 |
| 6,776,059 B2 | | 8/2004 | Kunimune et al. | |
| 6,872,573 B2 | | 3/2005 | Albarella et al. | |
| 2001/0019821 A1 | * | 9/2001 | Smith | ................. 435/5 |
| 2003/0224523 A1 | * | 12/2003 | Thornberg et al. | ............. 436/43 |
| 2006/0281188 A1 | * | 12/2006 | Mann et al. | .................... 436/169 |
| 2007/0161927 A1 | * | 7/2007 | Daugirdas | ..................... 600/573 |
| 2009/0011452 A1 | * | 1/2009 | Hoover | ............................ 435/29 |
| 2009/0070046 A1 | * | 3/2009 | Kenjou et al. | ................... 702/19 |
| 2009/0119130 A1 | * | 5/2009 | Kimmel et al. | ................... 705/3 |

FOREIGN PATENT DOCUMENTS

| | | |
|---|---|---|
| EP | 1022566 A2 | 7/2000 |
| EP | 1258732 A1 | 11/2002 |
| JP | 61-178663 A | 8/1986 |
| JP | 6-050957 A | 2/1994 |
| JP | 08075727 A * | 3/1996 |
| JP | 6-504874 A | 5/1997 |
| JP | 09-196909 A | 7/1997 |
| JP | 10213584 A * | 8/1998 |
| JP | 2000-105238 A | 4/2000 |
| JP | 2000-214169 A | 8/2000 |
| JP | 2001-249136 A | 9/2001 |
| JP | 2002-267662 A | 9/2002 |
| KR | 10-2000-0065930 | 11/2000 |
| KR | 10-2001-0002857 | 1/2001 |
| WO | WO-95/13543 A1 | 5/1995 |
| WO | WO-96/04554 A1 | 2/1996 |
| WO | WO-99/02983 A1 | 1/1999 |
| WO | WO 02/14832 A1 | 2/2002 |
| WO | WO-2006/138292 A2 | 12/2006 |
| WO | WO 2007123245 A1 * | 11/2007 |
| WO | WO-2009/078950 A2 | 6/2009 |

OTHER PUBLICATIONS 24 hour urine sodium output measurement, 1984-2013 Thomson Micromedex.*
Biological variation in analyte concentrations in urine of apparently healthy men and women, Clin Chem. Jun. 1987;33(6):847-50.*
Overnight Urine Collections to Estimate Sodium Intake, vol. 4, No. 4, Jul.-Aug. 1982.*
A simple method to estimate populational 24-h urinary sodium and potassium excretion using a casual urine specimen, J Hum Hypertens. Feb. 2002;16(2):97-103.*
Barr, D. B., et al., "Urinary Creatinine Concentrations in the U.S. Population: Implications for Urinary Biologic Monitoring Measurements", *Environmental Health Perspectives*, 113(2), (2005), 192-200.
Brungel, M., et al., "Evaluation of various rapid chloride tests for assessing urinary NaCl excretion.", *Ann. Nutr. Metab.*, 45, (2001), 169-174.
Luft, F. C., et al., "Compliance to a low-salt diet.", *Am J Clin Nutr.*, 65(2 Suppl), (Feb. 1997), 698S-703S.

(Continued)

*Primary Examiner* — Carol S Tsai
(74) *Attorney, Agent, or Firm* — Schwegman Lundberg & Woessner, P.A.

(57) ABSTRACT

Methods and kits of the invention are useful for calculating 24-hour excretion of sodium without the need to collect urine for 24 hours.

51 Claims, No Drawings

(56) References Cited

OTHER PUBLICATIONS

"U.S. Appl. No. 11/451,285, Restriction Requirement mailed Aug. 24, 2009", 8 pgs.
"European Application Serial No. 06773018.4 , Supplementary European Search Report mailed Feb. 18, 2009", 10 pgs.
"European Application Serial No. 06773018.4, Communication mailed Jul. 7, 2009", 1 pg.
"International Application Serial No. PCT/US06/22962, International Search Report mailed Dec. 31, 2007", 2 pgs.
"International Application Serial No. PCT/US06/22962, Written Opinion mailed Dec. 31, 2007", 3 pgs.
"International Application Serial No. PCT/US2008/013636, International Search Report mailed Jul. 30, 2009", 4 pgs.
"International Application Serial No. PCT/US2008/013636, Written Opinion mailed Jul. 30, 2009", 5 pgs.
Bingham, S. A., et al., "Reference values for analytes of 24-h urine collections known to be complete", *Ann. Clin. Biochem.*, 25, (1988), 610-619.
Boegehold, M. A., et al., "Importance of Dietary Chloride for Salt Sensitivity of Blood Pressure", *Hypertension*, 17(*Suppl I*), (1991), I-158-I-161.
Khaw, K-T., et al., "Blood pressure and urinary sodium in men and women: the Norfolk cohort of the European Prospective Investigation into Cancer (EPIC-Norfolk)", *Am. J. Clin. Nutr.*, 80, (2004), 1397-1403.
Knuiman, J. T., et al., "A multi-centre study on within-person variability in the urinary excretion of sodium, potassium, calcium, magnesium and creatinine in 8 European centres", *Human Nutrition: Clinical Nutrition*, 40C(5), (1986), 343-348.
Kunkel, M. E., et al., "Protein Intake and Urinary Excretion of Protein-Derived Metabolites in Aging Female Vegetarians and Nonvegetarians", *Journal of the American College of Nutrition*, 10(4), (1991), 308-314.
Luft, F. C., et al., "Overnight Urine Collections to Estimate Sodium Intake", *Hypertension*, 4, (1982), 494-498.
Morgan, T. O., "The effect of potassium and bicarbonate ions on the rise in blood pressure caused by sodium chloride", *Clinical Science*, 63, (1982), 407s-409s.
Pugia, M. J., et al., "Comparison of Instrument-Read Dipsticks for Albumin and Creatinine in Urine With Visual Results and Quantitative Methods", *Journal of Clinical Laboratory Analysis*, 12, (1998), 280-284.
Pugia, M. J., et al., "Comparison of Urine Dipsticks with Quantitative Methods for Microalbuminuria", *Eur. J. Clin. Chem. Clin. Biochem.* 35(9), (1997), 693-700.
Sloan, P. J. M., et al., "The Quantab Strip in the Measurement of Urinary Chloride and Sodium Concentrations", *Clinical Chemistry*, 30(10), (1984), 1705-1707.
Sugita, O., et al., "Reference values of serum and urine creatinine, and of cretinine clearance by a new enzymatic method", *Ann. Clin. Biochem.* 29, (1992), 523-528.
"U.S. Appl. No. 11/451,285, Response filed Jun. 10, 2010 to Non Final Office Action mailed Jan. 12, 2010", 9 pgs.
"Canadian Application Serial No. 2611906, Amendment and Response filed Jul. 8, 2010 to Communication dated Jan. 8, 2010", 15 pgs.
"European Application Serial No. 065773018.4, Response filed Jun. 2, 2010 to Communication dated Jan. 28, 2010", 16 pgs.
"U.S. Appl. No. 11/451,285 Non Final Office Action Mailed Jan. 12, 2010", 6.
"U.S. Appl. No. 11/251,285 Response filed Oct. 21, 2009 to Restriction Requirements mailed Aug. 24, 2009", 11 pgs.
"Canadian Application Serial No. 2611906, Office Action mailed Jan. 8, 2010", 8 pgs.
"European Application Serial No. 06773018.4, Communication mailed Jan. 28, 2010", 3 pgs.
"European Application Serial No. 06773018.4, Response filed Nov. 6, 2009 to Communication mailed Jul. 7, 2009", 24 pgs.
Truchaud, A., et al., "Parallel Evaluation of Astra 8 and Astra 4 Multichannel Analyzers in Two Hospital Laboratories", *Clinical Chemistry*, 26(1), (1980), 139-141.
"U.S. Appl. No. 11/451,285 Final Office Action mailed Aug. 18, 2010", 7 pgs.
"U.S. Appl. No. 11/451,285, Response flied Dec. 20, 2010 to Final Office Action mailed Aug. 18, 2010", 10 pgs.
"Canadian Application Serial No. 2,611,906, Response filed Feb. 7, 2011 to Office Action dated Aug. 6, 2010", 8 pgs.
"Canadian Application Serial No. 2611906, Office Action mailed Aug. 6, 2010", 3 pgs.
"European Application Serial No. 06773018.4, Office Action mailed Mar. 10, 2011", 4 pgs.
"Japanese Application Serial No. 2008-517011, Office Action mailed Feb. 28, 2011", (w/ English Translation), 5 pgs.
"Canadian Application Serial No. 2611906, Notice of Allowance Oct. 11, 2011", 2 pgs.
"European Application Serial No. 06773018.4, Response filed Jun. 27, 2011 to Office Action mailed Mar. 10, 2011", 33 pgs.
"Japanese Application Serial No. 2008-517011, Amendment and Argument filed May 26, 2011 in Response to Office Action mailed Feb. 28, 2011", (w/ English Translation), 19 pgs.
"Japanese Application Serial No. 2008-517011, Response filed May 26, 2011 to Office Action mailed Feb. 28, 2011", (w/ English Translation), 19 pgs.
"Japanese Application No. 2008-517011_Office Action_Jan. 23, 2012", 5 Pgs.
Kawasaki, T., et al., "A simple method for estimating 24 h urinary sodium and potassium excretion from second morning voiding urine specimen in adults", Clin Exp Pharmacol Physiol., 20(1), (Jan. 1993), 7-14.
Kawasaki, Terukazu, et al., "Estimation of 24-hour Urinary Sodium(Na) and Potassium(K) Excretion from Predicted Creatinine and Na(orK)/Creatinine Ratio for Second Morning Voiding Urine", J. Health Sci., 10, (1988), 115-120.
Ohta, Y., et al., "Long-term compliance with salt restriction in Japanese hypertensive patients", Hypertens Res., 28(12), (Dec. 2005), 953-7.
"U.S. Appl. No. 11/451,285, Non Final Office Action mailed Jun. 14, 2012", 8 pgs.
"European Application Serial No. 06773018.4, Office Action mailed Jun. 28, 2012", 6 pgs.
"European Application Serial No. 08861680, Amended Claims filed Jul. 13, 2010", 7 pgs.
"International Application Serial No. PCT/US06/22962, International Preliminary Report on Patentability dated Feb. 12, 2008", 4 pgs.
"International Application Serial No. PCT/US2008/013636, International Preliminary Report on Patentability mailed Jun. 24, 2010", 8 pgs.
"Japanese Application No. 2008-517011, Written Amendment and Argument filed Apr. 15, 2013 in Response to Office Action mailed Jan. 16, 2013", (w/ English Translation), 19 pgs.
"Japanese Application Serial No. 2008-517011, Office Action mailed Jan. 16, 2013", (w/ English Translation), 6 pgs.
"U.S. Appl. No. 11/451,285, Final Office Action mailed Oct. 18, 2012", 8 pgs.
"U.S. Appl. No. 11/451,285, Response filed Sep. 14, 2012 to Non Final Office Action mailed Jun. 14, 2012", 12 pgs.
"European Application Serial No. 06773018.4, Response filed Oct. 10, 2012 to Office Action mailed Jun. 28, 2012", 16 pgs.
"U.S. Appl. No. 11/451,285 , Response filed Jan. 17, 2013 to Final Office Action mailed Oct. 18, 2012", 13 pgs.
"U.S. Appl. No. 11/451,285, Non Final Office Action mailed Oct. 15, 2013", 8 pgs.
"Japanese Application Serial No. 2008-517011, Examiners Decision of Final Refusal mailed Jan. 27, 2014", With English Translation, 4 pgs.
"European Application Serial No. 08861680.0, Supplementary European Search Report mailed Oct. 25, 2013", 6 pgs.

\* cited by examiner

ID METHOD OF DETERMINING EXCRETION OF SODIUM AND OTHER ANALYTES

This application claims priority to U.S. Provisional Application Ser. No. 61/007,708, filed Dec. 14, 2007, and to U.S. Provisional Application Ser. No. 61/007,707, filed Dec. 14, 2007, the contents of which applications are specifically incorporated herein by reference in their entireties.

This application is related to U.S. patent application Ser. No. 11/451,285 filed Jun. 12, 2006 and PCT Application Ser. No. PCT/US2006/022962 filed Jun. 13, 2006, the contents of which applications are specifically incorporated herein by reference in their entireties.

FIELD OF THE INVENTION

The invention generally relates to methods, kits and nomograms for estimating 24-hour urinary excretion of sodium by a subject from a spot urine sample i.e., a sample obtainable from a single micturition or voiding.

BACKGROUND

Salt intake is of major importance in cardiovascular disease, particularly hypertension and congestive heart failure. Yet neither doctors nor patients have a convenient way to assess it. As a result, despite its importance, salt intake is rarely monitored. Diet histories are generally very unreliable, and subjects' estimation of their salt intake tends to bear little resemblance to their actual intake.

Currently available methods of estimating salt intake involve measurement of the volume of a collection of a subject's total urine specimens over a 24-hour period and determination of the sodium concentration in the urine collection to allow for calculation of the sodium excretion (i.e. urine volume×sodium concentration). Such urine collections are cumbersome, and offer many obstacles to adequate monitoring of sodium intake. Such obstacles involve delays in obtaining and analyzing the sample, incomplete collection of all urine generated in the 24 hour period of time, inconvenience for repeated or frequent monitoring, and the considerable variation in day-to-day sodium intake. As a result of these obstacles, sodium intake goes largely unmonitored even though routine assessment of sodium intake is of considerable medical importance.

SUMMARY OF THE INVENTION

The invention addresses long-standing problems existing in the available methods for determining sodium excretion by providing easy to use methods, kits and nomograms for determining the amount of sodium excreted by a subject over 24 hours without the need for a 24 hour collection of urine or a blood test. Moreover, the inventive methods, in some cases, provide more accurate results than existing methods that require 24 hour collection of urine. In addition, the methods of the invention permit serial monitoring of sodium intake, which cannot easily be done using currently available procedures.

One aspect of the invention method of determining a subject's 24-hour urinary excretion of an analyte from a single sample of the subject's urine, comprising:
measuring the analyte concentration in the single urine sample;
measuring creatinine concentration in the single urine sample;

using the subject's age, gender, race, weight, muscle mass, lean body mass, muscle mass, adiposity, physical activity, or a combination thereof, to select a normalized 24-hour creatinine excretion value from an array of normalized 24-hour creatinine excretion values, wherein each normalized 24-hour creatinine excretion value is an estimated mean of observed 24-hour urine creatinine concentrations for a population of persons of similar age, gender, race, weight, muscle mass, lean body mass, muscle mass, adiposity, and/or physical activity; and
using the normalized 24-hour creatinine excretion value, the measured analyte concentration, and the measured creatinine concentration to determine the 24-hour urinary excretion of analyte for the subject.

The 24-hour urinary excretion of a variety of analytes can be determined using the methods of the invention, including, for example, sodium chloride, albumin, catecholamine, calcium, methylmalonic acid, zinc, magnesium, n-terminal telopeptide (NTx) or a combination thereof.

In some embodiments, the 24-hour urinary excretion of analyte for the subject is determined by identifying the subject's 24-hour analyte excretion from an array of 24-hour urinary analyte excretion values that vary depending upon values for normalized 24-hour creatinine excretion, measured urinary analyte concentration, and measured urinary creatinine concentration.

In other embodiments, the 24-hour urinary excretion of the analyte for the subject is determined using the following formula:

$$\frac{\text{sample[analyte]} \times \text{normalized 24 hr creatinine value}}{\text{sample [creatinine]}} = \text{subject's 24-hr analyte excretion}$$

wherein:
sample [analyte] is the measured concentration of analyte in the subject's single urine sample;
sample [creatinine] is the measured concentration of creatinine in the subject's single urine sample;
normalized creatinine value is the normalized 24-hour creatinine excretion value; and
subject's 24-hour analyte excretion is the determined amount of analyte excreted by the subject over 24 hours.

According to the invention, the subject's gender, race and weight often have a larger impact on normalized 24-hour creatinine excretion values than other factors. Therefore, in some embodiments, the subject's gender, race and weight are used to select the normalized 24-hour creatinine excretion value from the array of normalized 24-hour creatinine excretion values. Similarly, in some embodiments, each normalized 24-hour creatinine excretion value is an estimated mean (from regression analysis) of observed 24-hour urine creatinine concentrations for a population of persons of similar gender, race, and weight.

According to the invention, improved results are obtained if the single urine sample is obtained approximately half-way through the subject's waking cycle, and several hours after a significant meal. For example, the single urine sample is conveniently obtained in late afternoon or early evening, before the evening meal.

The single urine sample can be obtained by the subject at home or work, the concentrations are measured by the subject at home or work and the subject's 24-hour urinary analyte excretion is determined by the subject at home or work. Similarly, the single urine sample can be obtained by the subject at any location, while the concentrations are measured by a health care professional and the subject's 24-hour urinary analyte excretion is determined by a health care professional.

In some embodiments, measurement of the analyte concentration and/or the creatinine concentration is quantitative. Alternatively, measurement of the analyte concentration and/or the creatinine concentration can be semi-quantitative. Thus, measurement of the analyte concentration and/or the creatinine concentration can yield a numerical value or a range of numerical values. Similarly, the determined 24-hour urinary excretion of analyte for the subject can be a numerical value or a range of numerical values. In addition, the determined 24-hour urinary excretion of analyte for the subject can also be an indication that the 24-hour urinary excretion of analyte for the subject is low, medium or high.

The analyte and/or creatinine concentrations in the urine sample can be measured using laboratory equipment and procedures. For example, procedures involving amperometry, fluorimetry, spectrometry, nuclear magnetic resonance, atomic emission spectrometry, atomic absorption spectrometry, gravimetry, titrimetry, colorimetry, enzyme linked immunosorbant assay (ELISA), high pressure liquid chromatography (HPLC), spectrometry, colorimetry, gas chromatography, mass spectrometry, enzymatic assay, electrophoretically or a combination thereof, can be used for measuring analyte and/or creatinine concentrations.

In other embodiments, the analyte concentration and/or the creatinine concentrations are measured without the use of a laboratory instrument. For example, the analyte concentration and/or the creatinine concentration in the subject's urine can be measured using a dipstick. Such dipstick measurements can yield numerical values. In other embodiments, the measurement of the analyte concentration and/or the creatinine concentration with a dipstick yields a colorimetric readout.

According to the invention an array of normalized 24-hour creatinine excretion values can be calculated using, for example, either of the following formulae:

$$y = 1150 \text{ mg} - 407.4 \text{ mg(if female)} + (5.7)(\text{weight in pounds}) - 88 \text{ mg(if white)} \quad \text{I}$$

$$y = 654 \text{ mg} - 537.3 \text{ mg(if female)} + (7.3)(\text{weight in pounds}) - 59.3 \text{ mg(if white)} \quad \text{II}$$

wherein y is a normalized 24-hr creatinine excretion value in milligrams.

Another aspect of the invention is a method of determining a subject's 24-hour urinary excretion of sodium from a single sample of the subject's urine, comprising: (a) measuring chloride concentration in the single urine sample; (b) measuring creatinine concentration in the single urine sample; (c) using the subject's age, gender, race, weight, muscle mass, lean body mass, muscle mass, adiposity, physical activity, or a combination thereof, to select a normalized 24-hour creatinine excretion value from an array of normalized 24-hour creatinine excretion values, wherein each normalized 24-hour creatinine excretion value is an estimated mean (from a regression analysis) of observed 24-hour urine creatinine concentrations for a population of persons of similar age, gender, race, weight, muscle mass, lean body mass, muscle mass, adiposity, and/or physical activity; and (d) using the normalized 24-hour creatinine excretion value, the measured chloride concentration, and the measured creatinine concentration to determine the 24-hour urinary excretion of sodium for the subject. Use of the normalized 24-hour creatinine excretion value obviates the need for 24 hour collections of urine.

In some embodiments, the 24-hour urinary excretion of sodium for the subject is determined by identifying the subject's 24-hour sodium excretion from an array of 24-hour urinary sodium excretion values that vary depending upon values for normalized 24-hour creatinine excretion, the measured chloride concentration, and the measured creatinine concentration.

In other embodiments, the 24-hour urinary excretion of sodium for the subject is determined using the following formula:

$$\frac{\text{sample [chloride]} \times \text{normalized 24 hr creatinine value}}{\text{sample [creatinine]}} \approx \text{subject's 24-hr sodium excretion}$$

wherein:

sample [chloride] is the measured concentration of chloride in the subject's single urine sample;

sample [creatinine] is the measured concentration of creatinine in the subject's single urine sample;

normalized creatinine value is the normalized 24-hour creatinine excretion value; and subject's 24-hour sodium excretion is the determined amount of sodium excreted by the subject over 24 hours.

According to the invention, the subject's gender, race and weight often have a larger impact on normalized 24-hour creatinine excretion values than other factors. Therefore, in some embodiments, the subject's gender, race and weight are used to select the normalized 24-hour creatinine excretion value from the array of normalized 24-hour creatinine excretion values. Similarly, in some embodiments, each normalized 24-hour creatinine excretion value is an estimated mean (from regression analysis) of observed 24-hour urine creatinine concentrations for a population of persons of similar gender, race, and weight.

Also according to the invention, single urine samples collected approximately half-way through the waking cycle, and several hours after a significant meal, often yield more accurate results when determining 24 hour sodium excretion values. For example, for people who typically work, or are awake, during the day, urine samples collected in late afternoon, before an evening meal and several hours after consuming the last meal, often yield optimal results. Hence, in some embodiments the single (spot) urine sample is obtained shortly before the evening meal. The single urine sample can be obtained by the subject at home or work. Similarly, the concentrations of chloride and creatinine can also be measured by the subject at home and the subject's 24-hour urinary sodium excretion can be determined by the subject at home or work. In other embodiments, the single urine sample is obtained by the subject at any location but the concentrations of chloride and creatinine in the urine are measured by a health care professional and the subject's 24-hour urinary sodium excretion is determined by a health care professional.

Measurement of the chloride concentration and/or the creatinine concentration can be quantitative or semi-quantitative. For example, measurement of the chloride concentration and/or the creatinine concentration can yield a numerical value or a range of numerical values.

Similarly, the determined 24-hour urinary excretion of sodium for the subject can be a numerical value or a range of numerical values. Alternatively, the determined 24-hour urinary excretion of sodium for the subject can be an indication that the 24-hour urinary excretion of sodium for the subject is low, medium or high.

The chloride concentration can be measured using a variety of methods and different types of equipment, for example, using amperometry, fluorimetry, spectrometry, nuclear magnetic resonance, atomic emission spectrometry, atomic absorption spectrometry, gravimetry, titrimetry, or colorimetry. The creatinine concentration also can be measured using a variety of methods and equipment, for example, by enzyme linked immunosorbant assay (ELISA), high pressure liquid chromatography (HPLC), spectrometry, colorimetry, gas chromatography, mass spectrometry, enzymatic assay, or electrophoretically.

In other embodiments, the chloride concentration and/or the creatinine concentration are measured without the use of a laboratory instrument. For example, the chloride concentration and/or the creatinine concentration in the subject's urine can be measured using a dipstick. Such a dipstick measurement of the chloride concentration and/or the creatinine concentration can yield a numerical value and/or a colorimetric readout.

In some embodiments, the array of normalized 24-hour creatinine excretion values used in the methods and kits of the invention is calculated using the following either of the formulae:

$$y = 1150 \text{ mg} - 407.4 \text{ mg(if female)} + (5.7)(\text{weight in pounds}) - 88 \text{ mg(if white)} \quad \text{I}$$

$$y = 654 \text{ mg} - 537.3 \text{ mg(if female)} + (7.3)(\text{weight in pounds}) - 59.3 \text{ mg(if white)} \quad \text{II}$$

wherein y is a normalized 24-hr creatinine excretion value in milligrams. In other embodiments, the array of normalized 24-hour creatinine excretion values that can be used in the methods of the invention is, for example, a table. One such table is:

| Weight | White males | Black males | White females | Black females |
|---|---|---|---|---|
| 90  |      |      | 1168 | 1256 |
| 100 |      |      | 1225 | 1313 |
| 110 | 1689 | 1777 | 1282 | 1370 |
| 120 | 1746 | 1834 | 1339 | 1427 |
| 130 | 1803 | 1891 | 1396 | 1484 |
| 140 | 1860 | 1948 | 1453 | 1541 |
| 150 | 1917 | 2005 | 1510 | 1598 |
| 160 | 1974 | 2062 | 1567 | 1655 |
| 170 | 2031 | 2119 | 1624 | 1712 |
| 180 | 2088 | 2176 | 1681 | 1769 |
| 190 | 2145 | 2233 | 1738 | 1826 |
| 200 | 2202 | 2290 | 1795 | 1883 |
| 210 | 2259 | 2347 | 1852 | 1940 |
| 220 | 2316 | 2404 | 1909 | 1997 |
| 230 | 2373 | 2461 | 1966 | 2054 |
| 240 | 2430 | 2518 | 2023 | 2111 |
| 250 | 2487 | 2575 | 2080 | 2168 |
| 260 | 2544 | 2632 | 2137 | 2225 |
| 270 | 2601 | 2689 | 2194 | 2282 |
| 280 | 2658 | 2746 | 2251 | 2339 |

Another aspect of the invention is a method of improving the accuracy of determining 24-hour urinary excretion of sodium by a subject from a single urine sample, comprising: (a) measuring creatinine concentration and chloride concentration in a single urine sample obtained from a subject in late afternoon before consuming a meal; (b) using the subject's gender, race and weight to select a normalized 24-hour creatinine excretion value from an array of normalized 24-hour creatinine excretion values, wherein each normalized 24-hour creatinine excretion value in the array is an estimated mean (from regression analysis) of observed 24-hour urine creatinine concentrations for a population of persons with the subject's gender, race and weight; and (c) determining the subject's 24-hour urinary excretion of sodium.

For example, the subject's 24-hour urinary excretion of sodium can be determined using the following formula:

$$\frac{\text{sample[chloride]} \times \text{normalized 24 hr creatinine value}}{\text{sample [creatinine]}} \approx \text{subject's 24-hr sodium excretion}$$

wherein:
sample [chloride] is the measured concentration of chloride in the subject's single urine sample;
sample [creatinine] is the measured concentration of creatinine in the subject's single urine sample;
normalized creatinine value is the normalized 24-hour creatinine excretion value; and
the subject's 24-hour sodium excretion is the determined amount of sodium excreted by the subject over 24 hours.

Alternatively, the subject's 24-hour sodium excretion can be determined from a table reciting an array of estimated or calculated 24-hour excretion values.

Another aspect of the invention is a kit for determining or calculating 24-hour excretion of sodium by a subject, the kit comprising: (a) a container for holding a spot urine sample; (b) a device for measuring chloride concentration in the spot urine sample; (c) a device for measuring creatinine concentration in the spot urine sample; and (d) instructions comprising:
  a first nomogram listing normalized 24-hour creatinine excretion values for distinct populations of subjects, where the normalized 24-hour creatinine excretion values vary depending upon the populations' age, gender, race, weight, lean body mass, muscle mass, adiposity, physical activity, or a combination thereof, and
  a second nomogram listing calculated 24-hour sodium excretion values, where the calculated 24-hour sodium excretion values are derived from the normalized 24-hour urine creatinine excretion value for the subject, the chloride concentration in the spot urine sample and the creatinine concentration in the spot urine sample.

Devices for measuring chloride and creatinine concentrations in the spot urine sample can include any available device or collection of devices that can measure chloride and/or creatinine concentrations in urine. For example, such devices can be titrator dipsticks for colorimetric determination of the concentrations of chloride and creatinine in the urine sample. In some embodiments, the first nomogram is a listing of normalized 24-hour creatinine excretion values that vary depending upon the populations' gender, race, and weight. For example, the first nomogram of the kit can be a table of 24-hour sodium excretion values for various populations of people (see, e.g., Table 1).

An example of a second nomogram listing calculated 24-hour sodium excretion values is provided herein as Table 6 (see Example 2).

Another aspect of the invention is an article of manufacture comprising an array of normalized 24-hour creatinine excretion values and instructions for converting a subject's spot urine chloride concentration and the subject's spot urine creatinine concentration to a normalized 24 hour sodium concentration for the subject. For example, the instructions can include directions for obtaining the sodium concentration and the creatinine concentration. Devices for measuring the chloride concentration and the creatinine concentration can also be included in the article of manufacture. One array of normalized 24-hour creatinine excretion values that can be included in the article of manufacture is, for example, the array shown in Table 1.

Another aspect of the invention is a computer-readable medium having stored thereon an array of normalized 24-hour creatinine excretion values and a program of instructions executable by a processor to convert a subject's urine sample chloride concentration value, and the subject's urine sample creatinine concentration to a calculated 24 hour sodium concentration for the subject.

The invention is directed to a method of estimating 24-hour urinary excretion of sodium from a spot urine by obtaining a spot urine sample from a subject, determining chloride concentration in the spot urine sample, determining creatinine concentration in the spot urine sample, selecting a normalized value for estimated 24-hour urine creatinine excretion from an array of normalized values, based upon the subject's age, gender, race, weight, muscle mass, lean body mass, muscle mass, adiposity, physical activity, or a combination thereof, and selecting a normalized value for estimated 24-hour sodium excretion from an array of normalized values, based upon the normalized value for estimated 24-hour urine creatinine excretion, the chloride concentration and the creatinine concentration. In some embodiments, the spot urine sample is obtained at a specific time of day, identified as late afternoon or early evening and before the evening meal.

Yet another aspect of the present invention is directed to a kit for calculating 24-hour excretion of sodium by a subject. The kit comprises a container for holding a spot urine sample, a device for measuring chloride concentration in the spot urine sample, a device for measuring creatinine concentration in the spot urine sample, and instructions comprising a first nomogram for selecting a normalized 24-hour creatinine excretion value based upon the subject's age, gender, race, weight, lean body mass, muscle mass, adiposity, physical activity, or a combination thereof, and a second nomogram for selecting the subject's calculated 24-hour sodium excretion value based upon the normalized value for estimated 24-hour urine creatinine excretion, the measured chloride concentration and the measured creatinine concentration.

DETAILED DESCRIPTION OF THE INVENTION

The present invention enables individuals to accurately estimate the amount of sodium excreted in their urine during a 24-hour period of time without the need for a 24-hour collection of urine, or taking blood samples. In some embodiments, extensive laboratory analysis of the urine sample is also avoided. Such an accurate estimation of 24-hour sodium excretion is an excellent measure of the individual's sodium intake. By quickly and easily monitoring 24-hour sodium excretion levels using the methods of the invention an individual or health care worker can readily monitor whether the individual's sodium intake is acceptable, or whether the individual needs to adjust his or her intake of sodium. In addition, the methods of the invention permit serial monitoring of sodium intake, which cannot easily be done using currently available procedures.

The invention relates to kits and nomograms for rapid, convenient, easy-to-use and inexpensive estimation of sodium excretion. The invention also relates to a method, which employs easy-to-use nomograms, and which can be performed using the kit. The methods, kits and nomograms simplify conversion of data relating to an actual measurement of chloride concentrations in a single sample of urine into an accurate estimation of 24-hour excretion of sodium by the subject who provided the urine sample. Such methods, kits and nomograms of the invention can be used as often as desired by a physician, nurse or a physician's technician in evaluating a subject's sodium intake both at a health care facility. Alternatively, the methods and kits of the invention can be used by any individual without the need for a doctor visit, for example, at home, or anywhere where the individual may choose to monitor his or her sodium intake.

The development of a set of easy-to-use nomograms provides a simple method for adjustment of a subject's measured chloride/creatinine ratio, which enables estimation of the 24-hour excretion of sodium by the subject with much greater accuracy than has been possible without the adjustment.

Pursuant to the invention, nomograms are used to adjust the ratio of chloride and creatinine concentrations in a single (spot) urine sample by employing pre-determined "normalized" 24-hour creatinine excretion values for a population of persons or animals with one or more characteristics of the subject from which the urine sample was obtained. Characteristics that can influence sodium excretion, and which the nomograms of the invention address, include, for example, age, gender, race, weight, lean body mass, muscle mass, adiposity, physical activity, or any combination thereof. It has also been discovered that the predictive accuracy of the methods and kits of the invention for use in determining sodium excretion can be increased by obtaining the spot urine sample in the late afternoon or early evening, before the evening meal.

The methods of the invention for accurately estimating 24-hour urinary excretion of sodium from a spot urine sample involve the following general steps. After obtaining a spot urine sample, the concentration of both the chloride and the creatinine in the spot urine sample is determined. Then, a normalized value for 24-hour urine creatinine excretion is selected from an array of such normalized values. The normalized 24-hour urine creatinine excretion values in the array can be obtained from a nomogram, where each value is a product of an equation that takes into account variables that affect 24-hour urine creatinine excretion including, for example, the subject's age, gender, race, weight, muscle mass, lean body mass, muscle mass, adiposity, physical activity, or a combination thereof. Thus, each population of subjects with the same age, gender, race, weight, muscle mass, lean body mass, muscle mass, adiposity, and/or physical activity, has the same normalized value of 24-hour creatinine excretion. The mass of creatinine excreted by a subject not afflicted with any substantial challenge to homeostasis can be expected to remain reasonably constant over time. In other words, for any individual with stable renal function, the 24-hour urinary creatinine excretion is relatively constant from day to day. The mass of creatinine excreted by a subject with impaired renal function is also relatively constant from day-to-day, provided the impairment in renal function is stable.

In some embodiments, the factors employed to determine the normalized 24-hour excretion values of creatinine include subject's age, gender, race, weight, muscle mass, lean body mass, muscle mass, adiposity, physical activity, or a combination thereof. In other embodiments, the factors employed to determine the normalized 24-hour excretion values of creatinine include subject's age, gender, race, weight, muscle mass, lean body mass, muscle mass, physical activity, or a combination thereof. In other embodiments, the factors employed to determine the normalized 24-hour excretion values of creatinine include subject's age, gender, race, weight, muscle mass, lean body mass, muscle mass, or a combination thereof. In other embodiments, the factors employed to determine the normalized 24-hour excretion values of creatinine include subject's age, gender, race, weight, muscle mass, or a combination thereof. In other embodiments, the factors employed to determine the normalized 24-hour excretion values of creatinine include subject's age, gender, race, weight, or a combination thereof. In other embodiments, the factors employed to determine the normalized 24-hour excretion values of creatinine include subject's age, gender, race, weight, adiposity, physical activity, or a combination thereof.

To determine the subject's sodium excretion, the method of the invention conveniently provides a nomogram of 24-hour sodium excretion values where the 24-hour sodium excretion value has been calculated based upon the normalized value for estimated 24-hour urine creatinine excretion determined in the previous step, the measured chloride concentration for the subject and the measured creatinine concentration for the subject.

Thus, the methods of the invention are more convenient than those currently available because the inventive methods require only a single urine sample, whereas currently available methods generally require the subject to collect all urine generated over a 24-hour period of time. Even though the methods of the invention require only one sample of urine, the sodium excretion of the subject is accurately assessed from the concentration of chloride in the urine relative to the concentration of creatinine in the same urine sample, where this chloride/creatinine ratio is converted to the amount of sodium excreted over 24-hours using a pre-determined, normalized 24-hour creatinine excretion value as a correction factor.

The methods of the invention are more accurate than previously available ratiometric methods because those previously available methods fail to consider the fact that the amount of creatinine excreted in 24 hours, although constant from day to day for any given individual, differs considerably between individuals. Thus, for example, a 100 pound woman might have a urine creatinine excretion of 900 mg/day, whereas a 250 pound male might have a urine creatinine of 2500 mg. Unless such between-person variability in creatinine excretion is corrected, ratios that rely upon creatinine to correct for differences in urine filtration rates are a poor measure of sodium excretion.

Because of this considerable between-person variance in 24 hour urine creatinine excretion, to accurately estimate the 24-hour excretion of sodium from an chloride/creatinine ratio, the ratio must be adjusted to take into account the amount of creatinine typically excreted by that individual in 24-hours. The usual method of determining 24-hour creatinine excretion is a 24-hour urine collection. However, 24-hour collections of urine are plagued by the impracticality of collecting urine for 24 hours and by inaccuracy in many cases due to undercollection of urine.

The methods and kits of the invention obviate the need for 24-hour collections of urine. Instead, normalized 24-hour creatinine values that are calculated as described herein are used as correction factors. Moreover, use of these normalized 24-hour creatinine excretion values is actually more accurate than relying upon actual collection of urine by the subject. This is because the normalized creatinine excretion values correlate more closely with muscle mass (the source of creatinine) than does an actual (often incomplete) 24 hour collection of urine.

Actual collection of all urine over a 24-hour period of time is compromised by incomplete collection, as well as day-to-day variations in diet and exercise. Problems relating to incomplete collection, and variations in diet and exercise give rise to 10-15%, or greater, variation in the amount of creatinine measured in a 24-hour collection of urine. In contrast, the normalized 24-hour creatinine excretion values of the invention are accurately corrected to take into account the effects of varying body weight, gender, race, age, muscle mass, lean body mass, muscle mass, adiposity, physical activity, or a combination thereof. Accordingly, as discovered by the inventors, each subpopulation of subjects with the same or similar gender, race, age, weight, and muscularity will have the same normalized 24-hour creatinine excretion value— and this value is often a more accurate estimation of the subject's 24-hour creatinine excretion than that obtained using an actual 24-hour collection of urine.

Thus, the invention includes normalized values for 24-hour urine creatinine excretion for various populations and subpopulations of subjects, as well as simple instructions for adjustment of measured chloride/creatinine ratios using those normalized 24-hour urine creatinine excretion values. For example, normalized 24 hour creatinine values for white and black males and females who have different weights are provided in Table 1.

TABLE 1

Normalized 24 Hour Creatinine Values in Milligrams For Different Subjects

| Weight | White males | Black males | White females | Black females |
|---|---|---|---|---|
| 90 | | | 1168 | 1256 |
| 100 | | | 1225 | 1313 |
| 110 | 1689 | 1777 | 1282 | 1370 |
| 120 | 1746 | 1834 | 1339 | 1427 |
| 130 | 1803 | 1891 | 1396 | 1484 |
| 140 | 1860 | 1948 | 1453 | 1541 |
| 150 | 1917 | 2005 | 1510 | 1598 |
| 160 | 1974 | 2062 | 1567 | 1655 |
| 170 | 2031 | 2119 | 1624 | 1712 |
| 180 | 2088 | 2176 | 1681 | 1769 |
| 190 | 2145 | 2233 | 1738 | 1826 |
| 200 | 2202 | 2290 | 1795 | 1883 |
| 210 | 2259 | 2347 | 1852 | 1940 |
| 220 | 2316 | 2404 | 1909 | 1997 |
| 230 | 2373 | 2461 | 1966 | 2054 |
| 240 | 2430 | 2518 | 2023 | 2111 |
| 250 | 2487 | 2575 | 2080 | 2168 |
| 260 | 2544 | 2632 | 2137 | 2225 |
| 270 | 2601 | 2689 | 2194 | 2282 |
| 280 | 2658 | 2746 | 2251 | 2339 |

These and other normalized 24-hour creatinine excretion values are obtained by observing how much creatinine is excreted over 24 hours in different populations of individuals, for example, in subjects of different body weight, age, gender, race, muscle mass, lean body mass and/or level of physical activity. To derive a normalized creatinine 24-hour normalized value for different populations of individuals, 24-hour urine samples are collected from the different populations of individuals. For each 24-hour sample obtained from the population, the concentration of creatinine in the sample is determined. The total amount of creatinine in the 24 hour collection is determined by multiplying the total volume of the urine sample by the concentration of creatinine—this is the total amount of creatinine excreted by the subject from which the urine sample was obtained.

However, according to the invention, the accuracy of data obtained from 24-hour urine collections should be scrutinized and steps should be taken to guard against under-collection. To guard against under-collection, 24-hour creatinine excretion values that were below 1300 mg/day in males or below 600 mg/day in females are deemed to be from incomplete collections and are not included in the deriving regression formulae used to generate normalized 24-hour creatinine excretion values. Where such formulae are refined with a larger number of subjects, any 24-hour creatinine excretion value that is <20 mg/kg in males or <15 mg/kg in females is rejected as being an incomplete collection.

A normalized 24-hour creatinine excretion value for a population of individuals with the same gender, sex, age, muscle mass, lean body mass and/or level of physical activity is readily calculated by regression analysis of the total 24-hour creatinine values for tested individuals in that population. Exemplary formulae I and/or II are used for obtaining normalized 24-hour creatinine excretion values:

$$y=1150 \text{ mg} - 407.4 \text{ mg(if female)} + (5.7)(\text{weight in pounds}) - 88 \text{ mg(if white)} \qquad \text{I}$$

$$y=654 \text{ mg} - 537.3 \text{ mg(if female)} + (7.3)(\text{weight in pounds}) - 59.3 \text{ mg(if white)} \qquad \text{II}$$

wherein: y is the normalized 24-hr creatinine excretion value in milligrams (mg). Formula II was generated using a larger pool of subjects. However, either formula yields acceptable normalized 24-hour creatinine excretion values.

It will be appreciated that the artisan can readily refine these formulae to include additional variables (e.g., age, ethnicity such as Asian, Caucasian or African, lean muscle mass, adiposity, or level of physical activity), accumulating data on each variable, and deriving therefrom, by well-known methods of regression analysis, more powerful regression formulae. However, as described herein, major factors affecting creatinine excretion include body weight, gender and race. Accordingly, the normalized 24-hr creatinine excretion values listed in Table 1 permit highly accurate determinations of the amounts of sodium excreted by a subject over 24 hours.

The foregoing formulae can be used for determining normalized 24-hour creatinine excretion values for different populations by calculation using the equation, by use of a computer program, and/or by use of a look-up table or a nomogram. To facilitate sodium excretion determinations by a variety of people, a nomogram is preferred because it can be used without the need for calculations by the subject. Such exemplary nomograms or look-up tables for a normalized 24-hour creatinine excretion values are shown in Table 1 and Table 12, where the values in these tables were derived by regression analysis of the mass of creatinine found in actual 24-hour collections of urine.

A subject can readily determine his or her 24-hour excretion of sodium in few simple steps: first, by consulting the table of normalized 24-hour creatinine excretion values (e.g., Table 1) and selecting a normalized 24-hour creatinine excretion value corresponding to the individual's weight, sex, race, gender, etc., and second, by using the selected normalized 24-hour creatinine excretion value along with the values measured for chloride and creatinine concentration in the individual's spot urine sample, to solve the following equation:

$$\text{Subject's Sodium Excretion} \approx \frac{(\text{Normalized 24 hr Creatinine value from Table}) \times (\text{Chloride Conc.})}{(\text{Creatinine Conc.}) \times 10}$$

Again, the equation can be solved, without limitation, by hand, or by means of a computer program, a look-up table or a nomogram. By way of example and not of limitation, Table 6 of Example 2 is a look-up table for finding 24-hour sodium excretion by individuals. The user, for example, may determine from Table 1 that his/her normalized 24-hour creatinine excretion is 2000 mg. To obtain the determined 24-hour excretion of sodium, the user selects the page corresponding to 2000 mg from Table 6, and then identifies his/her determined 24-hour sodium excretion level by locating the column corresponding to the value measured for creatinine concentration in his/her urine sample, and the row corresponding to the measured urinary chloride concentration. As is clear from this example, the method enables the user, whether patient, technician or physician, to easily calculate the 24-hour sodium excretion from the spot urine chloride and creatinine concentrations, by correction using the individual's normalized 24-hour creatinine excretion value.

The accuracy of the methods of the invention for measuring sodium intake is increased when an accurate normalized value for 24-hour creatinine excretion is selected to fit the subject according to the subject's weight, gender, ethnicity, etc., and this normalized value is used to adjust the chloride/creatinine ratio. Without wishing to be bound by a particular theory, a method that employs normalized 24-hour urine creatinine values is thought to improve the accuracy of determining 24-hour sodium excretion when using the measured chloride/creatinine ratio for a subject, because different amounts of creatinine are excreted by different individuals, depending to a large extent on the muscle mass of the individual, which is the source of creatinine. Since weight, gender and ethnicity are prominent determinants of total muscle mass, and are readily recorded, the methods described herein can be used to determine normalized 24-hour creatinine excretion values for different populations of people.

Use of the normalized 24-hour creatinine excretion values avoids the need for drawing blood samples, for measurements of urine volume, and for 24 hour urine collections, while adding precision to raw chloride/creatinine ratios that have been measured for individual subjects. The normalized values for 24-hour creatinine employed herein thus take into account between-person differences in creatinine excretion, require no urine collection, and, unlike actual 24-hour urine collections, the accuracy of these values does not suffer from incomplete collections. Each subpopulation of subjects with the same or similar gender, race, age, weight, and muscularity will have the same normalized 24-hour creatinine excretion value.

These normalized 24-hour creatinine excretion values are used in the methods of the invention to adjust the measured chloride/creatinine ratio of a subject to permit more accurate determination of the amount of chloride excreted by that subject in 24 hours. Without correction for gender, race, weight, etc., people having similar chloride/creatinine ratios would be expected to excrete similar amounts of chloride over 24 hours. However, when these chloride/creatinine ratios are adjusted by correcting for the fact that different people excrete different amounts of creatinine, then it becomes apparent that, for example, a chloride/creatinine ratio obtained from a small female who typically excretes only 900 mg of creatinine per day is actually exhibiting three-fold lower chloride excretion levels than the same ratio obtained in a large male who excretes 2700 mg/day of creatinine. Correction involving use of normalized 24-hour creatinine excretion values for subpopulations of people eliminates such overestimation.

Analyte/creatinine ratios have been employed for estimating the urinary excretion of certain analytes. However, these ratios are obtained without adjustment using normalized 24-hour creatinine values and are therefore often erroneous. A recent study reported that 85 of 138 subjects who tested positive for high albumin/creatinine ratio turned out to be false positives, when compared to results of determination from the 24-hour urine collection (Hypertension 47:56, 2006). The positive predictive value in such a study was only 38.4%. False positives were particularly prevalent among those with a low 24-hour urine creatinine excretion, particularly women. Another study found a 30% false positive rate among those over the age of 65 (Amer J Kidn Dis 39:1183, 2002). These studies demonstrate the inaccuracy of the ratio if it is not indexed to the actual 24-hour urine creatinine excretion of the individual, or to a reasonable estimate thereof.

A convenient assessment of urinary creatinine excretion in spot urine samples, adjusted for estimated 24-hour creatinine excretion, would have other medical uses. For example, people who form recurrent kidney stones and need to increase their urine volume could readily use the nomogram and/or formulae described herein to determine 24-hour urine volume from a single urine sample through easy arithmetic modifications of the creatinine levels measured in the sample using the nomogram. This could revolutionize medical management of patients with kidney stones, as increasing urine output is the most important intervention in preventing recurrent stones. Based on the nomogram, a desired urine creatinine concentration, indicative of 24-hour volume, could be recommended by the patient's physician and the patient could monitor compliance at home by using the method and kit of the invention.

The nomogram could also be used in elderly people who are prone to hyponatremia (abnormally low blood sodium concentrations) and need to restrict fluid intake and urine output, by assisting them in maintaining a urine concentration above a certain level as determined by their physicians.

Urine Samples

According to the invention, 24 hour excretion of sodium by a subject can be determined from a single sample of urine. A spot (single) urine sample is therefore obtained from a subject, where the sample volume is sufficient to fill one or two small test tubes. For example, for many chloride and creatinine measurement procedures, the urine sample need only be a volume of about 15-30 mL.

In certain preferred embodiments, sodium excretion, which directly reflects sodium intake, is estimated from a spot urine sample collected at a time of day when the within-subject day-to-day variance of creatinine excretion is minimal. In this connection, for maximum predictive power, data for use in embodiments of the invention should not be acquired after ingesting a meal containing a high amount of protein, because such a meal transiently increases creatinine excretion. In a highly preferred embodiment of the invention, the method is applied to a spot urine sample collected in the late afternoon, preferably a few hours after lunch and before the evening meal.

It is well-known that within-subject variations in sodium and chloride excretion, which occur throughout the day, can affect the ability to determine 24-hour sodium excretion from a spot urine sample. In this connection, it has been discovered that a spot sample collected during the late afternoon approximates the 24-hour sodium excretion rate, particularly because it occurs approximately in the middle of the 24-hour collection period. As a result, the effect of a sodium excretion rate that is either increasing or decreasing throughout the day is minimized by sampling the urine at the midpoint of the 24-hour period.

Accordingly, in many embodiments, improved 24-hour sodium excretion determinations are obtained when urine samples are obtained in later afternoon or early evening, before the subject ingests an evening meal.

Determining 24-Hour Excretion Values of Other Analytes

The methods and nomograms described herein can also be used to significantly improve estimation of excretion of any other analyte excreted in urine. In particular, as described herein the 24-hour normalized excretion values for creatinine provide a useful normalizing value that can be used with measured analyte/creatinine ratio obtained from a spot sample of urine. Such methods are easy to use. Examples include, but are not limited to, estimation of: (1) 24-hour calcium excretion from a urine calcium/creatinine ratio, particularly for subjects at risks of developing or suffering from kidney stones; (2) 24-hour catecholamine excretion from a urine catecholamine/creatinine ratio to screen a subject for pheochromocytoma; (3) 24-hour methylmalonic acid excretion from a methylmalonic acid/creatinine ratio for determining vitamin B12 deficiency; (5) 24-hour NTx excretion from a NTx/creatinine ratio for monitoring osteoporosis; and (6) 24-hour albumin excretion from a ratio of albumin/creatinine. Analytes of interest include, for example, but without limitation, albumin, catecholamine, calcium, methylmalonic acid, zinc, magnesium and n-terminal telopeptide (NTx). Of course convenient assessment of excretion of many other analytes is also possible using the methods of the invention, assuming that the analyte is excreted in the urine and is amenable to measurement and calculation from a spot urine analyte/creatinine ratio.

Just as sodium excretion can be accurately estimated from the normalized 24-hour creatinine excretion values determined herein, estimation of excretion of any other analyte's excretion levels over 24-hours can be determined. For example, the 24-hour excretion of an analyte from an analyte/creatinine ratio can be obtained from a spot urine sample using the following equation:

$$\text{24-hr analyte excretion}(mEq) = \frac{\text{sample[analyte]}\,(mEq/L) \times \text{24-hr normalized creatinine excretion value(mg)}}{\text{sample [cretinine]}\,(mg/dL) \times 10}$$

The concentration of analytes of interest are measured in spot urine samples to estimate 24-hour urinary excretion of such analytes. Such concentrations can be determined using any available procedure. For example, laboratory equipment and/or analyzers can be used to determined analyte concentrations. Such laboratory equipment and laboratory detection procedures can include amperometry, fluorimetry, spectrometry, nuclear magnetic resonance, atomic emission spectrometry, atomic absorption spectrometry, gravimetry, titrimetry, colorimetry, enzyme linked immunosorbant assay (ELISA), high pressure liquid chromatography (HPLC), spectrometry, colorimetry, gas chromatography, mass spectrometry, enzymatic assay, electrophoretically or a combination thereof. For example, zinc and other atoms can be measured using atomic absorption procedures.

Bioassay Systems (Hayward Calif.) provides assay kits for a variety of analytes, including albumin, cations and anions such as calcium, chloride, magnesium and zinc.

Alternatively, portable detection devices such as dipsticks can also be employed. For example, calcium levels can be measured using a kit from Diagnostic Systems Laboratories (Webster, T X; see Zerwekh & Nicar, Clin. Chem. 30(3): 452-453 (984)) and the Microalbustix™ sticks (Siemens Corp.) can be used to measure albumin levels. U.S. Pat. No. 5,948,632 also described methods and reagents for measuring calcium in aqueous solutions.

Urinary concentrations of catecholamines can be measured by available methods, for example, the fluorometric methods of Viktora, Baukal and Wolff, Anal. Biochem. 28: 513 (1968). U.S. Pat. No. 4,288,542 also describes methods for measuring catecholamines in urine.

Methylmalonic acid levels in urine can be measured using any available method, for example, the commercially available radioligand kit (Bio-Rad, Diagnostics Group, Hercules, Calif.). Additional information on determining methylmalonic acid levels in urine is available, for example, as follows: Magera M J, Helgeson J K, Matern D, et al: Methylmalonic acid measured in plasma and urine by stable-isotope dilution and electrospray tandem mass spectrometry. Clin Chem 2000; 46:1804-1810; Klee G G: Cobalamin and folate evaluation: measurement of methylmalonic acid and homocysteine vs vitamin B(12) and folate. Clin Chem 2000; 46(8 Pt 2): 1277-1283; Snow C F: Laboratory diagnosis of vitamin B12 and folate deficiency: a guide for the primary care physician. Arch Intern Med 1999; 159(12):1289-1298; Norman E J & Morrison J A: Screening elderly populations for cobalamin (vitamin B12) deficiency using the urinary methylmalonic acid assay by gas chromatography mass spectrometry. Am J Med 1993; 94(6):589-594.

Chloride Measurement

To assess sodium intake, the concentration of chloride in a spot (single) urine sample is measured. Urinary chloride concentrations are measured, rather than directly determining sodium concentrations, because chloride serves as an accurate surrogate for sodium excretion, and also because there currently are no available methods that accurately measure sodium without somewhat elaborate equipment typically found in clinical and analytical laboratories. However, there are simple methods for accurately determining chloride concentrations that rely upon easily transported assay kits.

Chloride ions in aqueous samples can be analyzed by amperometry, fluorimetry, spectrometry, nuclear magnetic resonance, atomic emission spectrometry, atomic absorption spectrometry, gravimetry, titrimetry, or colorimetry. However, while many of these analytical methods are highly sensitive and precise, they frequently require expensive equipment and/or somewhat involved or complicated manipulations. While such methods can be employed for determining chloride in urine sample, they have certain drawbacks and are not ideal for measurement of chloride concentrations outside of an analytical laboratory or clinical setting.

However, simple, fast methods for measuring chloride are available. For example, U.S. Patent Publication 20060281188 describes various methods for detecting chloride in urine. Another example, involves assay procedures that rely upon the reaction of chloride with silver to generate a color change in a solid substrate containing the silver. Silver chromate, for example, is converted by chloride ion into white silver chloride, where the dark brown color of the silver chromate is changed to yellow in proportion to the amount of chloride ion in a test sample. Silver chromate in water produces a very unstable hydrophobic colloid. Thus, while silver chromate may be used in a solution or tablet, it is advantageous to use silver chromate in conjunction with a solid substrate. For example, an absorbent strip-like carrier such as filter paper can be used by impregnating the strip with a solution of silver chromate. Such a strip can then be used as one type of test dipstick for detection of chloride. U.S. Pat. No. 4,211,532, which is specifically incorporated by reference herein in its entirety, describes some of the factors to consider when making such a silver chromate test strip.

Chloride concentrations can also be accurately measured by adapting available procedures such as those described in U.S. Pat. No. 4,444,193, which provides a skin patch for use in the management of patients with cystic fibrosis ("CF"). The patch detects chloride above a pre-determined level in sweat (see also a similar but improved CF patch in U.S. Pat. No. 6,042,543). U.S. Pat. No. 4,650,768 describes a device comprising a porous matrix impregnated with silver salts and carrageenan. The device is said to be suitable for detecting chloride in urine. No suggestion is made, however, to use the device to measure chloride excretion, in conjunction with creatinine. U.S. Pat. No. 4,744,952 describes a "test paper" for determining the concentration of halogen ions (including chloride) in urine and other fluids. U.S. Pat. No. 5,229,299 describes a chloride test strip with a colorimetric readout that is not obscured by secondary products of the reaction (e.g., silver oxide). Its contemplated application is chloride detection in cement.

Commercially available test strips that accurately measure chloride can also be used, such as the Quantab™ Chloride Tritrator stick available from the Hach Company (Loveland, Colo.).

Creatinine Measurement

Creatinine concentrations are measured in urine samples because they provide an index of the rate at which water is filtered from the bloodstream into urine. The filtration rate varies depending on the physiological state of the subject, for example, variations in fluid intake affect filtration rate and, hence, the creatinine concentration in a subject's urine. Creatinine is a breakdown product of creatine, which is an important part of muscle. Creatinine cannot be used by cells and is excreted in the urine. The daily production of creatine, and subsequently creatinine, depends on muscle mass, which fluctuates very little in most normal people over long periods of time. Accordingly, the daily amount of creatinine excreted by subjects with similar muscle mass is similar. People with similar gender, weight, and race have similar muscle mass and therefore also excrete similar amounts of creatinine over a 24 hour period of time.

According to the invention, the amount of sodium excreted by a subject over 24 hours can be determined from the ratio of measured chloride:measured creatinine in a single sample of the subject's urine so long as that ratio is adjusted using a normalized value of 24-hour creatinine excretion for persons with a similar gender, weight and race. Such normalized 24-hour creatinine excretion values can be calculated as described herein. Table 1 provides normalized 24-hour creatinine excretion values for individuals of different race, gender and weight, three factors that most significantly affect creatinine excretion.

To assess the impact of fluid intake and/or filtration rate on the concentration of chloride in a subject's urine sample, the concentration of creatinine in the subject's urine sample is also measured. Any method for measuring creatinine levels in a urine sample can be employed in the methods of the invention. For example, creatinine concentrations can be measured using methods involving enzyme linked immunosorbant assay (ELISA), high pressure liquid chromatography (HPLC), spectrometry, colorimetry, gas chromatography, mass spectrometry, enzymatic assay, or electrophoresis (e.g., capillary or gel electrophoresis).

A number of chemistries have been developed to measure creatinine concentrations quantitatively in urine, blood plasma and other body fluids. For example, the Jaffe method can be used, which involves the formation of red-yellowish brown colored creatinine picrate by reaction of picric acid and creatinine in an alkaline solution. A more recent method for creatinine determination is reported by Benedict and Behre (J. Biol. Chem., 113:515 (1936)), which involves the reaction of 3,5-dinitrobenzoic acid (DNBA) with creatinine in an alkaline medium. Each of these reactions requires a high pH (i.e. greater than about 11.5 and typically from about 12 to about 14), in order to deprotonate the creatinine for the system to operate properly. Strongly basic substances such as alkali and alkaline earth metal hydroxides are typically used to maintain a suitably high pH in these reagent systems. U.S. Pat. No. 5,385,847 discloses a device that permits determination of urinary protein and creatinine in a reaction vessel where the protein is detected by immunoassay in a first reaction zone followed by the creatinine determination in a second reaction zone.

An exemplary chemistry, which can be used in a test strip format, was developed by Pugia, et al. (see., e.g., U.S. Pat. No. 5,374,561 and U.S. Pat. No. 6,001,656, both of which are specifically incorporated herein by reference in their entireties). U.S. Pat. No. 6,001,656 describes an assay for creatinine in urine in which the urine is contacted with a reagent system comprising cupric ions, a hydroperoxide and an oxidizable dye together with 4-hydroxy-2-methylquinoline. The 4-hydroxy-2-methylquinoline may be present in the reagent system at a concentration of from 10 to 300 mM, the hydroperoxide can be diisopropyl benzene dihydroperoxide and the oxidizable dye can be 3,3',5,5'-tetramethylbenzidine. Other methods for determining creatinine activity that may find use in the instant invention are described in the following: U.S. Pat. Nos. 5,610,073, 5,702,955, 5,733,787, 6,210,971, and 6,872,573, each of which is specifically incorporated herein by reference in its entirety.

In some embodiments, commercially available test strips can be used for measuring creatinine concentrations. For example, the Multistix PRO® Urinalysis Strips and the Microalbustix™ strips produced by Siemens Corporation (New York, N.Y.) are simple to use and provide useful semi-quantitative measurements of urinary creatinine concentrations. Another available method for measuring urinary creatinine involves use of the Clinitek 50™ urine chemistry analyzer (Siemens Corporation, New York, N.Y.).

Kits

Another aspect of the invention is a kit for estimating the 24-hour excretion of an analyte. The kit comprises a container for holding the spot urine sample; a device for measuring the concentration of the analyte in the spot urine sample; a device for measuring creatinine concentration in the spot urine sample; and instructions for use. In some embodiments, the instructions comprise a first nomogram (e.g., as illustrated by Table 1) for selecting a normalized 24-hour creatinine excretion value based upon the subject's age, gender, race, weight, lean body mass, muscle mass, adiposity, physical activity, or a combination thereof. The instructions can also include a second nomogram for selecting an estimated 24-hour analyte excretion value based upon the normalized value for estimated 24-hour urine creatinine excretion, the measured analyte concentration in the urine sample and the measured creatinine concentration in the urine sample.

The analyte can be any analyte detectable in urine, for example, sodium chloride, albumin, catecholamine, calcium, methylmalonic acid, zinc, magnesium and n-terminal telopeptide (NTx), or a combination thereof.

In one embodiment, the kit includes a titrator stick to measure urine analyte concentration(s), a titrator stick to measure urine creatinine concentration, a test tube or other container to hold the urine sample, and a booklet containing instructions and the nomogram(s).

Any container for holding the urine sample can be used, such as a test tube or a urine cup. In some embodiments, a cup is provided for collection of urine and a test tube is provided for measuring the analyte and creatinine concentrations in the urine. The urine sample is collected in the cup and a portion of the urine is transferred to test tube for testing.

Preferred embodiments in which patients may realize the objective of obtaining an estimate of their intake of an analyte as often as desired, and at low cost, by means of a simple urine test include, without limitation, any system of chemical reagents wherein the reagents react with the analyte or creatinine in a sample of urine to yield reaction products in amounts that are proportional to the concentration of analyte or creatinine in the urine. The amounts of analyte reaction product and/or creatinine reaction product should be distinguishable and easily read by eye. Moreover, the amounts of analyte reaction product and/or creatinine reaction product should reflect the amount of analyte or creatinine with at least semi-quantitative precision.

In some embodiments, the invention relates to a method of determining the 24 hour excretion of an analyte in the spot urine sample by separately measuring analyte and creatinine concentrations in the urine sample using separate test strips or dipsticks bearing reagents that react with analyte and creatinine, respectively. The test strips or dipsticks produce reaction products that can be read by spectrometry, preferably by producing a change in the color of the test strip or dipstick, which change can preferably be appreciated by the naked eye, at least semi-quantitatively.

In preferred embodiments, laboratory instruments are not required to determine the concentration of the analyte or creatinine, so the determination of 24-hour analyte excretion can be made by a subject at home or in any other non-clinical setting.

A number of chemistries have been derived to measure creatinine concentrations quantitatively in urine, including those described in U.S. Pat. Nos. 5,374,561, 5,610,073, 5,702,955, 5,733,787, 6,001,656, 6,210,971, and 6,872,573. Other currently available test strips for urinary creatinine are Multistix PRO Urinalysis Strips™ or Microalbustix™ strips that use a pad for creatinine, and a Clinitek 50™ urine chemistry analyzer (all from Siemens Corporation, New York, N.Y.).

Dipsticks for measurement of various analytes, as described herein. For example, chloride concentrations can be measure using commercially available dipsticks, such as Quantab Chloride Titrator™ strips (Hach Co, Loveland, Colo.).

Another aspect of the invention involves a kit and method of measuring analyte and creatinine concentrations in the urine sample simultaneously, not only for convenience but to maximize the accuracy of the analysis. An example of a device that measures chloride and creatinine is described in U.S. Pat. No. 5,710,372, incorporated herein by reference in its entirety. The solid-state device comprises a plurality of separate test regions spaced along an inert support, each test region comprising an inert matrix impregnated with a reagent selectively interactive with the analyte of interest. Another example is provided by U.S. Pat. No. 6,413,473, also incorporated herein in its entirety by reference. The teachings of these patents are included to provide guidance for making a test strips or dipsticks. U.S. patent application Ser. No. 11/451,285 describes such a strip specifically for use in determining chloride excretion.

Computer Readable Media

Another aspect of the invention is an article of manufacture such as a computer readable medium encoded with machine-readable data and/or a set of instructions, where the instructions can be carried out by a computer or a processing system. Such a computer readable medium can be a conventional compact disk read only memory (CD-ROM) or a rewritable medium such as a magneto-optical disk which is optically readable and magneto-optically writable. The computer readable medium can be prepared by available procedures. For example, the computable readable medium can have a suitable substrate (which may be conventional), and a suitable coating (which may also be conventional), usually on one side of the substrate.

In the case of CD-ROM, as is well known, a reflective coating can be employed that is impressed with a plurality of pits to encode the machine-readable data. The arrangement of pits is read by reflecting laser light off the surface of coating. A protective coating, which preferably is substantially transparent, is used on top of coating that has a plurality of pits.

In the case of a magneto-optical disk, as is well known, the coating has no pits, but has a plurality of magnetic domains whose polarity or orientation can be changed magnetically when heated above a certain temperature, as by a laser. The orientation of the domains can be read by measuring the polarization of laser light reflected from coating. The arrangement of the domains encodes data, for example, normalized 24-hour creatinine excretion values and/or an array of 24-hour urinary analyte (e.g., sodium or chloride) excretion values. The array of 24-hour urinary analyte (e.g., sodium or chloride) excretion values vary depending upon the normalized 24-hour creatinine excretion value, as well as the analyte and creatinine concentrations measured in subjects' urine, as described above.

Thus, in accordance with the present invention, data capable of facilitating determination of the amount of an analyte excreted by a subject over 24 hours is stored in a machine-readable storage medium. Executable code can also be included in the machine-readable medium that is capable of calculating a subject's 24-hour analyte excretion when the medium is used in conjunction with a computer or processor. For example, the machine readable medium, used in conjunction with a computer or processor can calculate a subject's 24-hour analyte excretion levels after an individual enters data relating to the subject's spot urine concentrations of analyte (e.g., chloride) and creatinine.

DEFINITIONS

The term "article of manufacture" as used herein refers to a kit or a computer readable medium (e.g., computer chip or magnetic storage medium such as hard disk drives, floppy disks, tape), optical storage medium (e.g., OD-ROMs, optical disks, etc.), volatile and non-volatile memory devices (e.g., EEPROMs, ROMs, PROMs, RAMs, DRAMs, SPAMs, firmware. programmable logic, etc.). Code and data (e.g., one or more nomograms) in the computer readable medium is accessed and executed by a processor. The code and/or data in which implementations are made may further be accessible through a transmission media or from a file server over a network. Of course, those skilled in the art will recognize that many modifications may be made to this configuration without departing from the scope of the implementations and that the article of manufacture may comprise any information bearing medium known in the art.

"Colorimetric" refers to any means of measurement or analysis wherein the qualitative or quantitative appreciation of color, or a change in color, whether discerned or appreciated visually or with the aid of instrumentation, is a factor in such measurement or analysis. The broader term "spectrometric" includes colorimetric determinations but extends to electromagnetic energies outside the visual spectrum that only instrumentation can detect.

"Concentration" refers to the amount of a substance admixed with a given amount of another substance or solvent.

The term "cumulative excretion" or simply "excretion" refers to the total mass of a substance excreted in the urine in a given amount of time. Accuracy of the measure can depend on complete collection of all urine excreted (typically in a "24-hour collection"), accurate measurement of the collected volume, and/or accurate measurement of the concentration of the substance in the collected urine.

The "diet" refers generally to the beverages and foodstuffs a subject voluntarily ingests by mouth. Herein, however, "intake" and "diet" may be used interchangeably even though "intake" could extend to parenteral (by-passing the gut) or rectal administration, stomach tube, etc. "Dietary salt intake" refers generally to sodium chloride, but may refer also to other salts.

A "dipstick," also referred to herein as a "titration stick," "titrator stick," "strip" or "test strip," comprises a "matrix," viz., any material capable of (1) being configured as a dipstick or test strip, (2) retaining by adsorption, absorption, sequestration or otherwise one or more elements that undergo a state-change in the presence of chloride or creatinine, and (3) permitting the chloride or creatinine to interact with said element(s) to yield said state-change. Measurement of the state-change amounts to a "read-out" of the concentration of the chloride or creatinine. It is preferred in this case that the elements that undergo state-change be chemical reagents retained in or on the matrix at least until such reagent(s) react in response to chloride or creatinine contacting said reagent(s) to yield a readable reaction product. Although preferred, the reaction product need not be retained on the test strip for the read-out. Although preferred, the reaction product need not be on the test strip when read out but in solution or on an "indicator strip," which indicator strip may be a separate strip or a separate part of a compound strip. A "readable" reaction product is a product susceptible to detection, preferably at a specific concentration or level of chemical activity within a range, by any means, including but not limited to calorimetric, electrometric, and spectrometric.

"Excessive salt intake" is any amount of salt (especially sodium chloride in this case) ingested or administered in a given period in excess of salt lost in perspiration, defecation, etc., and minimal excretion (about 2.5 to 4 grams per day in man). For the purposes of the instant invention, the terms "salt intake, "sodium intake," "salt excretion," or "sodium excretion" may each be used interchangeably.

A "laboratory" comprises instrumentation that enables at least the performance of the chemical analyses referred to herein but requires trained personnel for its operation and maintenance.

"Normalized" refers to data mathematically adjusted by a factor such that the elements of the factored dataset are more readily compared than the elements of the unfactored dataset. "Ratiometric" normalization obtains when two independent variables depend in common on a third variable; the ratio of the two independent variables tends to yield data devoid of variations attributable to the third variable.

A "patient" herein refers to a human or an animal, especially domestic and husbanded animals. The terms "patient" and "subject" are used interchangeably.

A chemical reaction is "read" by measuring the disappearance (specifically, the rate or degree of disappearance) of a reactant in the reaction or the appearance (the rate or degree of appearance) of a reaction product of the reaction. The measurement may be calibrated by means of a "reference standard," which is a pre-determined amount or concentration of a reactant or reaction product.

A "reagent" is a chemical substance, which becomes a reactant in a chemical reaction that results in a reaction product.

A "semi-quantitative" measure is one that approximates the quantity or amount of a substance and is considered between a qualitative and quantitative result.

A "surrogate" herein refers to an activity or amount of a chemical detected or measured to provide an estimate of another chemical activity or amount that is not actually measured.

A "single urine sample" or a "spot urine sample" is a sample of urine that leaves the body during urination and is of sufficient volume to permit determination of the concentration of chloride and creatinine within the sample. Unless otherwise indicated a "urine sample" is not a 24-hour collection of urine.

Terms such as "urine chloride" or "urinary creatinine" refer generally to the chemical concentration of the particular substance in a sample of urine. For purposes of the instant invention, however, such terms may refer, where the context so admits, to the total mass of the substance in a volume of urine.

The following non-limiting Examples illustrate aspects of the invention.

EXAMPLES

Certain embodiments of the invention, and data obtained in the development of those embodiments, are set out below to clarify aspects of the disclosure. These Examples are not intended to be limiting in any way.

Materials

Chloride concentration measurements were performed using Quantab Chloride Titrator™ strips (Hach Co, Loveland, Colo.), and creatinine concentration measurements were obtained using Microalbustix™ strips, which contain a pad for creatinine (Siemens Corp., New York, N.Y.). Other currently available test strips for urinary creatinine are Multistix PRO Urinalysis Strips™, which has a pad for creatinine, or a Clinitek 50™ urine chemistry analyzer (Siemens Corp., New York, N.Y.).

When a Hach Quantab™ test strip for chloride determinations is completely saturated with fluid, a moisture sensitive string across the top of the titrator typically turns brown to indicate that the reaction between chloride and the silver in the test strip is complete. The 0-10 scale on the strip is divided into easily read increments of 0.2. Thus, Quantab™ Hach Test Strips are semi-quantitative and are accurate to ±10 percent (Hach Company, Loveland, Colo.).

General Methods

Quantab™ chloride strips were placed into test tubes containing a spot urine sample and allowed to react until the indicator thread turned brown, indicating completion of the reaction. The height of the column on the numbered Quantab™ scale was read, and, using the conversion table, this value was converted into chloride concentration.

Creatinine sticks were dipped into the urine and then quickly removed. Excess urine was shaken off the strip. The stick was read at 60 seconds by comparing the color of the strip at 60 seconds with the color spectrum provided by the manufacturer, where different colors represent different creatinine concentrations. The concentration that most closely matched the color on the strip was then recorded.

Example 1

Correlation Between Dipstick Measurements and Laboratory Measurements

The strength of the correlation between dipstick measurement of chloride and laboratory measurement of both chloride and sodium was determined by Spearman's correlation coefficient. The correlation between creatinine values determined by dipstick and analytical laboratory methods was also assessed. Finally, the correlation between dipstick chloride/creatinine ratio and laboratory chloride/creatinine ratio was assessed.

Laboratory and dipstick measurements of chloride concentration and of chloride/creatinine ratio were categorized into tertiles (low, middle, high) to determine the degree of agreement between assessments. The number of subjects who were categorized to the same tertile by both laboratory and titrator stick methods was assessed by the Kappa statistic. The number of subjects categorized to the same tertile by dipstick chloride-creatinine ratio versus laboratory sodium-creatinine ratio was similarly assessed. Finally, categorization into tertiles based on chloride concentration alone was compared to categorization based on chloride/creatinine ratio, to confirm that chloride indexed to creatinine produces a value that clearly differs from measurement solely of chloride concentration.

Two-tailed probability levels for statistical significance tests are reported. Analyses were performed in SPSS Version 13.0 (SPSS Inc., Chicago, Ill.).

As shown in Tables 2-5 below, urinary chloride assessed by the dipstick method is remarkably consistent with laboratory chloride determination, and without question provides a valid and convenient alternative to laboratory measurements of urinary chloride. The results also indicate that urinary chloride closely approximates urinary sodium concentration, and therefore use of the chloride dipstick serves as a reliable surrogate for sodium measurement, for which there is no dipstick available.

The dipstick chloride/creatinine ratio also adequately approximated the laboratory chloride/creatinine and sodium/creatinine ratios, indicating that a dipstick chloride/creatinine ratio method can be used as an alternative to laboratory measurements of sodium/creatinine ratios.

Similarly, there was very highly significant agreement between the two methods with respect to categorization into low, medium, and high tertiles of dipstick and laboratory measurements of chloride concentration (Table 2) and of chloride-creatinine ratios (p<0.001, Table 3). Non-agreement was typically seen once per category, which may partly be due to the use of arbitrary cutoff values between tertiles. Thus, for example, no subjects had a high ratio by one method and low ratio by the other.

TABLE 2

Tertiles of Urinary Chloride Measured by Dipstick Compared to
Tertiles of Urinary Chloride Measured by Laboratory Methods

| Tertiles of Urinary Chloride Measured by Laboratory | Tertiles of Urinary Chloride Measured by Dipstick | | | |
| --- | --- | --- | --- | --- |
| | Low | Middle | High | Total |
| Low | 9 | 1 | 0 | 10 |
| Middle | 1 | 9 | 1 | 11 |
| High | 0 | 1 | 9 | 10 |
| Total | 10 | 11 | 10 | 31 |

Kappa = 0.8, p < 0.0001

Table 3 shows the same strong relationship between the chloride-creatinine ratio measured by dipstick and the sodium-creatinine ratio measured by laboratory.

TABLE 3

Tertiles of Urinary Chloride-Creatinine Ratio Measured
by Dipstick Compared to Tertiles of Urinary Chloride-Creatinine
Ratio Measured by Laboratory Methods

| Tertiles of Urinary Chloride-Creatinine Ratio by Laboratory | Tertiles of Urinary Chloride-Creatinine Ratio by Dipstick | | | |
| --- | --- | --- | --- | --- |
| | Low | Middle | High | Total |
| Low | 10 | 0 | 0 | 10 |
| Middle | 0 | 7 | 3 | 10 |
| High | 0 | 4 | 7 | 11 |
| Total | 10 | 11 | 10 | 31 |

Kappa = 0.7, p < 0.0001

Table 4 shows that urinary chloride-creatinine ratios measured by dipstick methods correlate with urinary sodium-creatinine ratios measured by laboratory methods.

TABLE 4

Tertiles of Urinary Chloride-Creatinine Ratio Measured
by Dipstick Compared to Tertiles of Urinary Sodium-Creatinine
Ratio Measured by Laboratory Methods

| Tertiles of Urinary Sodium-Creatinine Ratio by Laboratory | Tertiles of Urinary Chloride-Creatinine Ratio by Dipstick | | | |
| --- | --- | --- | --- | --- |
| | Low | Middle | High | Total |
| Low | 9 | 1 | 0 | 10 |
| Middle | 1 | 7 | 2 | 10 |
| High | 0 | 3 | 8 | 11 |
| Total | 10 | 11 | 10 | 31 |

Kappa = 0.7, p < 0.0001

Although both chloride concentrations and chloride/creatinine ratios varied directly with chloride concentration, the dipstick-measured-chloride concentration bore little relationship to the dipstick chloride/creatinine ratio (Table 5). Therefore, an analysis of chloride concentrations does not provide the same information as a determination of chloride/creatinine ratios. Instead, determination of chloride/creatinine ratios is one way to correct for variability in fluid intake and filtration rate.

TABLE 5

Tertiles of Urinary Chloride-Creatinine Ratio Measured by Dipstick
Compared to Tertiles of Urinary Chloride Measured by Dipstick

| Tertiles of Urinary Chloride by Dipstick | Tertiles of Urinary Chloride-Creatinine Ratio by Dipstick | | | |
| --- | --- | --- | --- | --- |
| | Low | Middle | High | Total |
| Low | 4 | 3 | 3 | 10 |
| Middle | 5 | 2 | 4 | 11 |
| High | 1 | 6 | 3 | 10 |
| Total | 10 | 11 | 10 | 31 |

Kappa = −0.07, p = 0.71

Example 2

Determining a Subject's 24-Hour Sodium Excretion

This Example describes one method of the invention for determining how much sodium is excreted by a subject in 24 hours.

1. Urine Measurements

A. Before the evening meal, and at least 3 hours after any strenuous exercise, a urine sample is collected into a cup. The urine is dispensed into a test tube, so that the tube is filled no more than halfway. The urine remaining in the cup can be submitted to the lab. If a 24-hour collection of urine is available, that 24-hour collection of urine is also submitted to the laboratory.

B. Chloride Measurement: A Quantab™ Chloride Tritrator stick is inserted into the test tube, and left for 5-10 minutes until the yellow string near the top turns brown, indicating completeness of reaction. While the subject is waiting, creatinine levels in the urine sample can be measured.

When the yellow string near the top turns dark brown, the highest point reached by the rising pale column is noted and the number corresponding to this highest point is recorded (e.g. 6.2 or 4.6, etc.) as the subject's chloride concentration.

C. Creatinine Measurement: Perform while waiting for the chloride stick to react. Dip a Multistix PRO® Urinalysis Strip into the tube containing the subject's urine sample and begin timing the dipstick reaction as the creatinine stick is completely immersed in the tube so that the colored creatinine determination pad is completely wet with urine. Remove the dipstick promptly. Remove excess urine by tapping the stick gently against the top of the tube while it is removed. Place the stick face up on a paper towel. As the time approaches 1 minute, hold the stick against the menu of colors provided by the manufacturer (Siemens Corp.) and, at exactly 1 minute, select the color that most closely matches the color of the wet creatinine pad. Record this creatinine concentration value.

2. Find the Subject's 24-Hour Urine Creatinine

Using Table 1 (reproduced below), select the column appropriate for the subject's sex and race (either white male, white female, black male, or black female), and the row closest to the subject's weight to identify the subject's normalized 24-hour urine creatinine value. Record this normalized 24-hour creatinine value.

TABLE 1

Normalized 24 Hour Creatinine Values For Different Subjects

| Weight | White males | Black males | White females | Black females |
|---|---|---|---|---|
| 90 |  |  | 1168 | 1256 |
| 100 |  |  | 1225 | 1313 |
| 110 | 1689 | 1777 | 1282 | 1370 |
| 120 | 1746 | 1834 | 1339 | 1427 |
| 130 | 1803 | 1891 | 1396 | 1484 |
| 140 | 1860 | 1948 | 1453 | 1541 |
| 150 | 1917 | 2005 | 1510 | 1598 |
| 160 | 1974 | 2062 | 1567 | 1655 |
| 170 | 2031 | 2119 | 1624 | 1712 |
| 180 | 2088 | 2176 | 1681 | 1769 |
| 190 | 2145 | 2233 | 1738 | 1826 |
| 200 | 2202 | 2290 | 1795 | 1883 |
| 210 | 2259 | 2347 | 1852 | 1940 |
| 220 | 2316 | 2404 | 1909 | 1997 |
| 230 | 2373 | 2461 | 1966 | 2054 |
| 240 | 2430 | 2518 | 2023 | 2111 |
| 250 | 2487 | 2575 | 2080 | 2168 |
| 260 | 2544 | 2632 | 2137 | 2225 |
| 270 | 2601 | 2689 | 2194 | 2282 |
| 280 | 2658 | 2746 | 2251 | 2339 |

3. Determination of the Subject's 24-Hour Sodium Excretion

Table 6 provides sodium excretion values for different populations of subjects. The 24-hour excretion level of sodium for a particular subject is found in Table 6 by noting the subjects' normalized 24-hour urine creatinine value (listed in the box at the top of each page), the measured amount of chloride in the subjects' urine and the measured amount of creatinine in the subjects' urine. To determine the amount of sodium excreted by a subject, the subject (or health care worker) selects the page of Table 6 that recites the normalized 24-hour urine creatinine closest to the subject's normalized 24-hour creatinine value (which was selected from Table 1). For example, if the subject's normalized 24-hour urine creatinine value is 1479 mg (determined by Table 1 above), the page reciting a normalized 24-hour creatinine excretion of 1500 mg is used.

The calculated 24-hour sodium excretion of the subject is determined by selecting the column that matches the creatinine concentration measured in the subject's urine sample, and the row that matches the chloride concentration measured in the subject's urine. Note that in Table 6, the medium or acceptable 24-hour sodium excretion levels are indicated in bold and by use of underlining. If a subject's 24-hour sodium excretion level is less than any of these medium or acceptable 24-hour sodium excretion levels, then the subject's intake of sodium is likely too low. If a subject's 24-hour sodium excretion level is greater than any of these medium or acceptable 24-hour sodium excretion levels, then the subject's intake of sodium is too high.

In instructions provided in a kit of the invention, the calculated sodium excretion values can be color-coded. For example, the calculated sodium excretion values in Table 6 can be color-coded green (low), yellow (medium), or red (high), to indicate whether the calculated sodium excretion levels are acceptable (low and/or medium excretion levels) or may be of concern (e.g., red, high excretion levels).

TABLE 6

| Stick Chloride | Stick Creatinine | | | | |
|---|---|---|---|---|---|
|  | 10 | 50 | 100 | 200 | 300 |
| 1000 mg 24-Hour Creatinine | | | | | |
| 2 | 40 | 20 | 10 | 7 | 5 |
| 2.2 | 44 | 22 | 11 | 7 | 6 |
| 2.4 | 52 | 26 | 13 | 9 | 7 |
| 2.6 | 56 | 28 | 14 | 9 | 7 |
| 2.8 | 64 | 32 | 16 | 11 | 8 |
| 3 | 72 | 36 | 18 | 12 | 9 |
| 3.2 | 80 | 40 | 20 | 13 | 10 |
| 3.4 | 88 | 44 | 22 | 15 | 11 |
| 3.6 | 100 | 50 | 25 | 17 | 13 |
| 3.8 | 108 | 54 | 27 | 18 | 14 |
| 4 | 120 | 60 | 30 | 20 | 15 |
| 4.2 | 128 | 64 | 32 | 21 | 16 |
| 4.4 | 140 | 70 | 35 | 24 | 18 |
| 4.6 | 152 | 76 | 38 | 25 | 19 |
| 4.8 | 168 | 84 | 42 | 28 | 21 |
| 5 | 180 | 90 | 45 | 30 | 23 |
| 5.2 | 196 | 98 | 49 | 33 | 25 |
| 5.4 | 212 | 106 | 53 | 35 | 27 |
| 5.6 | 232 | 116 | 58 | 39 | 29 |
| 5.8 | 252 | 126 | 63 | 42 | 32 |
| 6 | 272 | 136 | 68 | 45 | 34 |
| 6.2 | 296 | 148 | 74 | 49 | 37 |
| 6.4 | 320 | 160 | 80 | 54 | 40 |
| 6.6 | 347 | 174 | 87 | 58 | 44 |
| 6.8 | 380 | 190 | 95 | 62 | 48 |
| 7 | 412 | 206 | 103 | 69 | 52 |
| 7.2 | 448 | 224 | 112 | 75 | 56 |
| 7.4 | 492 | 246 | 123 | 82 | 62 |
| 7.6 | 540 | 270 | 135 | 90 | 68 |
| 7.8 | 592 | 296 | 148 | 100 | 74 |
| 8 | 656 | 328 | 164 | 110 | 82 |
| 8.2 | 724 | 362 | 181 | 121 | 91 |
| 8.4 | 812 | 406 | 203 | 135 | 102 |
| 8.6 | 908 | 454 | 227 | 151 | 114 |
| 8.8 | 1012 | 506 | 253 | 170 | 127 |
| 9 | 1128 | 564 | 282 | 189 | 141 |
| 1100 mg 24-Hour Creatinine | | | | | |
| 2 | 44 | 22 | 11 | 7 | 6 |
| 2.2 | 48 | 24 | 12 | 8 | 6 |
| 2.4 | 57 | 29 | 14 | 10 | 7 |
| 2.6 | 62 | 31 | 15 | 10 | 8 |
| 2.8 | 70 | 35 | 18 | 12 | 9 |
| 3 | 79 | 40 | 20 | 13 | 10 |
| 3.2 | 88 | 44 | 22 | 14 | 11 |
| 3.4 | 97 | 48 | 24 | 17 | 12 |
| 3.6 | 110 | 55 | 28 | 18 | 14 |
| 3.8 | 119 | 59 | 30 | 20 | 15 |
| 4 | 132 | 66 | 33 | 22 | 17 |
| 4.2 | 141 | 70 | 35 | 23 | 18 |
| 4.4 | 154 | 77 | 39 | 26 | 19 |
| 4.6 | 167 | 84 | 42 | 28 | 21 |
| 4.8 | 185 | 92 | 46 | 31 | 23 |
| 5 | 198 | 99 | 50 | 33 | 25 |
| 5.2 | 216 | 108 | 54 | 36 | 27 |
| 5.4 | 233 | 117 | 58 | 39 | 29 |
| 5.6 | 255 | 128 | 64 | 43 | 32 |
| 5.8 | 277 | 139 | 69 | 46 | 35 |
| 6 | 299 | 150 | 75 | 50 | 37 |
| 6.2 | 323 | 163 | 81 | 54 | 41 |
| 6.4 | 352 | 176 | 88 | 59 | 44 |
| 6.6 | 382 | 191 | 96 | 64 | 48 |
| 6.8 | 418 | 209 | 105 | 68 | 52 |
| 7 | 453 | 227 | 113 | 76 | 57 |
| 7.2 | 493 | 246 | 123 | 83 | 62 |
| 7.4 | 541 | 271 | 135 | 90 | 68 |
| 7.6 | 594 | 297 | 149 | 99 | 74 |
| 7.8 | 651 | 326 | 163 | 109 | 81 |
| 8 | 722 | 361 | 180 | 120 | 90 |
| 8.2 | 796.4 | 398.2 | 199 | 133 | 100 |
| 8.4 | 893.2 | 446.6 | 223 | 149 | 112 |
| 8.6 | 998.8 | 499.4 | 250 | 166 | 125 |
| 8.8 | 1113.2 | 556.6 | 278 | 186 | 139 |
| 9 | 1240.8 | 620.4 | 310 | 208 | 155 |

TABLE 6-continued

| Stick Chloride | Stick Creatinine | | | | |
|---|---|---|---|---|---|
| | 10 | 50 | 100 | 200 | 300 |

1200 mg 24-Hour Creatinine

| Stick Chloride | 10 | 50 | 100 | 200 | 300 |
|---|---|---|---|---|---|
| 2 | 48 | 24 | 12 | 8 | 6 |
| 2.2 | 53 | 26 | 13 | 8 | 7 |
| 2.4 | 62 | 31 | 16 | 11 | 8 |
| 2.6 | 67 | 34 | 17 | 11 | 8 |
| 2.8 | 77 | 38 | 19 | 13 | 10 |
| 3 | 86 | 43 | 22 | 14 | 11 |
| 3.2 | 96 | 48 | 24 | 16 | 12 |
| 3.4 | 106 | 53 | 26 | 18 | 13 |
| 3.6 | 120 | 60 | 30 | 20 | 15 |
| 3.8 | 130 | 65 | 32 | 22 | 16 |
| 4 | 144 | 72 | 36 | 24 | 18 |
| 4.2 | 154 | 77 | 38 | 25 | 19 |
| 4.4 | 168 | 84 | 42 | 28 | 21 |
| 4.6 | 182 | 91 | 46 | 30 | 23 |
| 4.8 | 202 | 101 | 50 | 34 | 25 |
| 5 | 216 | 108 | 54 | 36 | 27 |
| 5.2 | 235 | 118 | 59 | 40 | 29 |
| 5.4 | 254 | 127 | 64 | 42 | 32 |
| 5.6 | 278 | 139 | 70 | 47 | 35 |
| 5.8 | 302 | 151 | 76 | 50 | 38 |
| 6 | 326 | 163 | 82 | 54 | 41 |
| 6.2 | 355 | 178 | 89 | 59 | 44 |
| 6.4 | 384 | 192 | 96 | 64 | 48 |
| 6.6 | 416 | 208 | 104 | 70 | 52 |
| 6.8 | 456 | 228 | 114 | 74 | 57 |
| 7 | 494 | 247 | 124 | 83 | 62 |
| 7.2 | 538 | 269 | 134 | 90 | 67 |
| 7.4 | 590 | 295 | 148 | 98 | 74 |
| 7.6 | 648 | 324 | 162 | 108 | 81 |
| 7.8 | 710 | 355 | 178 | 119 | 88 |
| 8 | 787 | 394 | 197 | 131 | 98 |
| 8.2 | 869 | 434 | 217 | 145 | 109 |
| 8.4 | 974 | 487 | 244 | 162 | 122 |
| 8.6 | 1090 | 545 | 272 | 181 | 136 |
| 8.8 | 1214 | 607 | 304 | 203 | 152 |
| 9 | 1354 | 677 | 338 | 227 | 169 |

1300 mg 24-Hour Creatinine

| Stick Chloride | 10 | 50 | 100 | 200 | 300 |
|---|---|---|---|---|---|
| 2 | 52 | 26 | 13 | 8 | 7 |
| 2.2 | 57 | 29 | 14 | 9 | 7 |
| 2.4 | 68 | 34 | 17 | 12 | 8 |
| 2.6 | 73 | 36 | 18 | 12 | 9 |
| 2.8 | 83 | 42 | 21 | 14 | 10 |
| 3 | 94 | 47 | 23 | 16 | 12 |
| 3.2 | 104 | 52 | 26 | 17 | 13 |
| 3.4 | 114 | 57 | 29 | 20 | 14 |
| 3.6 | 130 | 65 | 33 | 21 | 16 |
| 3.8 | 140 | 70 | 35 | 23 | 18 |
| 4 | 156 | 78 | 39 | 26 | 20 |
| 4.2 | 166 | 83 | 42 | 27 | 21 |
| 4.4 | 182 | 91 | 46 | 31 | 23 |
| 4.6 | 198 | 99 | 49 | 33 | 25 |
| 4.8 | 218 | 109 | 55 | 36 | 27 |
| 5 | 234 | 117 | 59 | 39 | 29 |
| 5.2 | 255 | 127 | 64 | 43 | 32 |
| 5.4 | 276 | 138 | 69 | 46 | 34 |
| 5.6 | 302 | 151 | 75 | 51 | 38 |
| 5.8 | 328 | 164 | 82 | 55 | 41 |
| 6 | 354 | 177 | 88 | 59 | 44 |
| 6.2 | 385 | 192 | 96 | 64 | 48 |
| 6.4 | 416 | 208 | 104 | 70 | 52 |
| 6.6 | 451 | 226 | 113 | 75 | 57 |
| 6.8 | 494 | 247 | 124 | 80 | 62 |
| 7 | 536 | 268 | 134 | 90 | 67 |
| 7.2 | 582 | 291 | 146 | 98 | 73 |
| 7.4 | 640 | 320 | 160 | 107 | 80 |
| 7.6 | 702 | 351 | 176 | 117 | 88 |
| 7.8 | 770 | 385 | 192 | 129 | 96 |
| 8 | 853 | 426 | 213 | 142 | 107 |
| 8.2 | 941 | 471 | 235 | 157 | 118 |
| 8.4 | 1056 | 528 | 264 | 176 | 132 |
| 8.6 | 1180 | 590 | 295 | 196 | 148 |
| 8.8 | 1316 | 658 | 329 | 220 | 164 |
| 9 | 1466 | 733 | 367 | 246 | 183 |

1400 mg 24-Hour Creatinine

| Stick Chloride | 10 | 50 | 100 | 200 | 300 |
|---|---|---|---|---|---|
| 2 | 56 | 28 | 14 | 9 | 7 |
| 2.2 | 62 | 31 | 15 | 10 | 8 |
| 2.4 | 73 | 36 | 18 | 13 | 9 |
| 2.6 | 78 | 39 | 20 | 13 | 10 |
| 2.8 | 90 | 45 | 22 | 15 | 11 |
| 3 | 101 | 50 | 25 | 17 | 13 |
| 3.2 | 112 | 56 | 28 | 18 | 14 |
| 3.4 | 123 | 62 | 31 | 21 | 15 |
| 3.6 | 140 | 70 | 35 | 23 | 18 |
| 3.8 | 151 | 76 | 38 | 25 | 19 |
| 4 | 168 | 84 | 42 | 28 | 21 |
| 4.2 | 179 | 90 | 45 | 30 | 22 |
| 4.4 | 196 | 98 | 49 | 33 | 25 |
| 4.6 | 213 | 106 | 53 | 35 | 27 |
| 4.8 | 235 | 118 | 59 | 39 | 30 |
| 5 | 252 | 126 | 63 | 42 | 32 |
| 5.2 | 274 | 137 | 69 | 46 | 34 |
| 5.4 | 297 | 148 | 74 | 49 | 37 |
| 5.6 | 325 | 162 | 81 | 55 | 41 |
| 5.8 | 353 | 176 | 88 | 59 | 44 |
| 6 | 381 | 190 | 95 | 63 | 48 |
| 6.2 | 414 | 207 | 104 | 69 | 52 |
| 6.4 | 448 | 224 | 112 | 75 | 56 |
| 6.6 | 486 | 243 | 122 | 81 | 61 |
| 6.8 | 532 | 266 | 133 | 86 | 67 |
| 7 | 577 | 288 | 144 | 97 | 72 |
| 7.2 | 627 | 314 | 157 | 105 | 78 |
| 7.4 | 689 | 344 | 172 | 115 | 86 |
| 7.6 | 756 | 378 | 189 | 126 | 95 |
| 7.8 | 829 | 414 | 207 | 139 | 104 |
| 8 | 918 | 459 | 230 | 153 | 115 |
| 8.2 | 1014 | 507 | 253 | 169 | 127 |
| 8.4 | 1137 | 568 | 284 | 189 | 142 |
| 8.6 | 1271 | 636 | 318 | 211 | 159 |
| 8.8 | 1417 | 708 | 354 | 237 | 177 |
| 9 | 1579 | 790 | 395 | 265 | 197 |

1500 mg 24-Hour Creatinine

| Stick Chloride | 10 | 50 | 100 | 200 | 300 |
|---|---|---|---|---|---|
| 2 | 60 | 30 | 15 | 10 | 8 |
| 2.2 | 66 | 33 | 17 | 11 | 8 |
| 2.4 | 78 | 39 | 20 | 14 | 10 |
| 2.6 | 84 | 42 | 21 | 14 | 11 |
| 2.8 | 96 | 48 | 24 | 17 | 12 |
| 3 | 108 | 54 | 27 | 18 | 14 |
| 3.2 | 120 | 60 | 30 | 20 | 15 |
| 3.4 | 132 | 66 | 33 | 23 | 17 |
| 3.6 | 150 | 75 | 38 | 25 | 19 |
| 3.8 | 162 | 81 | 41 | 27 | 20 |
| 4 | 180 | 90 | 45 | 30 | 23 |
| 4.2 | 192 | 96 | 48 | 32 | 24 |
| 4.4 | 210 | 105 | 53 | 35 | 26 |
| 4.6 | 228 | 114 | 57 | 38 | 29 |
| 4.8 | 252 | 126 | 63 | 42 | 32 |
| 5 | 270 | 135 | 68 | 45 | 33 |
| 5.2 | 294 | 147 | 74 | 50 | 37 |
| 5.4 | 318 | 159 | 80 | 53 | 40 |
| 5.6 | 348 | 174 | 87 | 59 | 44 |
| 5.8 | 378 | 189 | 95 | 63 | 47 |
| 6 | 408 | 204 | 102 | 68 | 51 |
| 6.2 | 444 | 222 | 111 | 74 | 56 |
| 6.4 | 480 | 240 | 120 | 80 | 60 |
| 6.6 | 521 | 260 | 131 | 87 | 65 |
| 6.8 | 570 | 285 | 143 | 92 | 71 |
| 7 | 618 | 309 | 155 | 104 | 77 |
| 7.2 | 672 | 336 | 168 | 113 | 84 |
| 7.4 | 738 | 369 | 185 | 123 | 92 |
| 7.6 | 810 | 405 | 203 | 135 | 101 |
| 7.8 | 888 | 444 | 222 | 149 | 111 |
| 8 | 984 | 492 | 246 | 164 | 123 |
| 8.2 | 1086 | 543 | 272 | 181 | 136 |
| 8.4 | 1218 | 609 | 305 | 203 | 152 |
| 8.6 | 1362 | 681 | 341 | 226 | 170 |
| 8.8 | 1518 | 759 | 380 | 254 | 190 |
| 9 | 1692 | 846 | 423 | 284 | 212 |

TABLE 6-continued

| Stick Chloride | Stick Creatinine | | | | |
|---|---|---|---|---|---|
| | 10 | 50 | 100 | 200 | 300 |
| 1600 mg 24-Hour Creatinine | | | | | |
| 2 | 64 | 32 | 16 | 10 | 8 |
| 2.2 | 70 | 35 | 18 | 11 | 9 |
| 2.4 | 83 | 42 | 21 | 14 | 10 |
| 2.6 | 90 | 45 | 22 | 14 | 11 |
| 2.8 | 102 | 51 | 26 | 18 | 13 |
| 3 | 115 | 58 | 29 | 19 | 14 |
| 3.2 | 128 | 64 | 32 | 21 | 16 |
| 3.4 | 141 | 70 | 35 | 24 | 18 |
| 3.6 | 160 | 80 | 40 | 26 | 20 |
| 3.8 | 173 | 86 | 43 | 29 | 22 |
| 4 | 192 | 96 | 48 | 32 | 24 |
| 4.2 | 205 | 102 | 51 | 34 | 26 |
| 4.4 | 224 | 112 | 56 | 38 | 28 |
| 4.6 | 243 | 122 | 61 | 40 | 30 |
| 4.8 | 269 | 134 | 67 | 45 | 34 |
| 5 | 288 | 144 | 72 | 48 | 36 |
| 5.2 | 314 | 157 | 78 | 53 | 39 |
| 5.4 | 339 | 170 | 85 | 56 | 42 |
| 5.6 | 371 | 186 | 93 | 62 | 46 |
| 5.8 | 403 | 202 | 101 | 67 | 50 |
| 6 | 435 | 218 | 109 | 72 | 54 |
| 6.2 | 474 | 237 | 118 | 78 | 59 |
| 6.4 | 512 | 256 | 128 | 86 | 64 |
| 6.6 | 555 | 278 | 139 | 93 | 70 |
| 6.8 | 608 | 304 | 152 | 98 | 76 |
| 7 | 659 | 330 | 165 | 110 | 82 |
| 7.2 | 717 | 358 | 179 | 120 | 90 |
| 7.4 | 787 | 394 | 197 | 131 | 98 |
| 7.6 | 864 | 432 | 216 | 144 | 108 |
| 7.8 | 947 | 474 | 237 | 159 | 118 |
| 8 | 1050 | 525 | 262 | 175 | 131 |
| 8.2 | 1158 | 579 | 290 | 193 | 145 |
| 8.4 | 1299 | 650 | 325 | 216 | 162 |
| 8.6 | 1453 | 726 | 363 | 241 | 182 |
| 8.8 | 1619 | 810 | 405 | 271 | 202 |
| 9 | 1805 | 902 | 451 | 302 | 226 |
| 1700 mg 24-Hour Creatinine | | | | | |
| 2 | 68 | 34 | 17 | 11 | 9 |
| 2.2 | 75 | 37 | 19 | 12 | 9 |
| 2.4 | 88 | 44 | 22 | 15 | 11 |
| 2.6 | 95 | 48 | 24 | 15 | 12 |
| 2.8 | 109 | 54 | 27 | 19 | 14 |
| 3 | 122 | 61 | 31 | 20 | 15 |
| 3.2 | 136 | 68 | 34 | 22 | 17 |
| 3.4 | 150 | 75 | 37 | 26 | 19 |
| 3.6 | 170 | 85 | 43 | 28 | 21 |
| 3.8 | 184 | 92 | 46 | 31 | 23 |
| 4 | 204 | 102 | 51 | 34 | 26 |
| 4.2 | 218 | 109 | 54 | 36 | 27 |
| 4.4 | 238 | 119 | 60 | 40 | 30 |
| 4.6 | 258 | 129 | 65 | 43 | 32 |
| 4.8 | 286 | 143 | 71 | 48 | 36 |
| 5 | 306 | 153 | 77 | 51 | 38 |
| 5.2 | 333 | 167 | 83 | 56 | 42 |
| 5.4 | 360 | 180 | 90 | 60 | 45 |
| 5.6 | 394 | 197 | 99 | 66 | 49 |
| 5.8 | 428 | 214 | 107 | 71 | 54 |
| 6 | 462 | 231 | 116 | 77 | 58 |
| 6.2 | 503 | 252 | 126 | 83 | 63 |
| 6.4 | 544 | 272 | 136 | 91 | 68 |
| 6.6 | 590 | 295 | 148 | 99 | 74 |
| 6.8 | 646 | 323 | 162 | 105 | 81 |
| 7 | 700 | 350 | 175 | 117 | 88 |
| 7.2 | 762 | 381 | 190 | 128 | 95 |
| 7.4 | 836 | 418 | 209 | 139 | 105 |
| 7.6 | 918 | 459 | 230 | 153 | 115 |
| 7.8 | 1006 | 503 | 252 | 169 | 126 |
| 8 | 1115 | 558 | 279 | 186 | 139 |
| 8.2 | 1231 | 615 | 308 | 205 | 154 |
| 8.4 | 1380 | 690 | 345 | 230 | 173 |
| 8.6 | 1544 | 772 | 386 | 256 | 193 |
| 8.8 | 1720 | 860 | 430 | 288 | 215 |
| 9 | 1918 | 959 | 479 | 321 | 240 |
| 1800 mg 24-Hour Creatinine | | | | | |
| 2 | 72 | 36 | 18 | 11.7 | 9 |
| 2.2 | 79.2 | 39.6 | 19.8 | 12.6 | 9.9 |
| 2.4 | 93.6 | 46.8 | 23.4 | 16.2 | 11.7 |
| 2.6 | 100.8 | 50.4 | 25.2 | 16.2 | 12.6 |
| 2.8 | 115.2 | 57.6 | 28.8 | 19.8 | 14.4 |
| 3 | 129.6 | 64.8 | 32.4 | 21.6 | 16.2 |
| 3.2 | 144 | 72 | 36 | 23.4 | 18 |
| 3.4 | 158.4 | 79.2 | 39.6 | 27 | 19.8 |
| 3.6 | 180 | 90 | 45 | 29.7 | 22.5 |
| 3.8 | 194.4 | 97.2 | 48.6 | 32.4 | 24.3 |
| 4 | 216 | 108 | 54 | 36 | 27 |
| 4.2 | 230.4 | 115.2 | 57.6 | 37.8 | 28.8 |
| 4.4 | 252 | 126 | 63 | 42.3 | 31.5 |
| 4.6 | 273.6 | 136.8 | 68.4 | 45 | 34.2 |
| 4.8 | 302.4 | 151.2 | 75.6 | 50.4 | 37.8 |
| 5 | 324 | 162 | 81 | 54 | 40.5 |
| 5.2 | 352.8 | 176.4 | 88.2 | 59.4 | 44.1 |
| 5.4 | 381.6 | 190.8 | 95.4 | 63 | 47.7 |
| 5.6 | 417.6 | 208.8 | 104.4 | 70.2 | 52.2 |
| 5.8 | 453.6 | 226.8 | 113.4 | 75.6 | 56.7 |
| 6 | 489.6 | 244.8 | 122.4 | 81 | 61.2 |
| 6.2 | 532.8 | 266.4 | 133.2 | 88.2 | 66.6 |
| 6.4 | 576 | 288 | 144 | 96.3 | 72 |
| 6.6 | 624.6 | 312.3 | 156.6 | 104.4 | 78.3 |
| 6.8 | 684 | 342 | 171 | 110.7 | 85.5 |
| 7 | 741.6 | 370.8 | 185.4 | 124.2 | 92.7 |
| 7.2 | 806.4 | 403.2 | 201.6 | 135 | 100.8 |
| 7.4 | 885.6 | 442.8 | 221.4 | 147.6 | 110.7 |
| 7.6 | 972 | 486 | 243 | 162 | 121.5 |
| 7.8 | 1065.6 | 532.8 | 266.4 | 179.1 | 133.2 |
| 8 | 1180.8 | 590.4 | 295.2 | 197.1 | 147.6 |
| 8.2 | 1303.2 | 651.6 | 325.8 | 216.9 | 162.9 |
| 8.4 | 1461.6 | 730.8 | 365.4 | 243 | 182.7 |
| 8.6 | 1634.4 | 817.2 | 408.6 | 270.9 | 204.3 |
| 8.8 | 1821.6 | 910.8 | 455.4 | 305.1 | 227.7 |
| 9 | 2030.4 | 1015.2 | 507.6 | 340.2 | 253.8 |
| 1900 mg 24-Hour Creatinine | | | | | |
| 2 | 76 | 38 | 19 | 12 | 10 |
| 2.2 | 84 | 42 | 21 | 13 | 10 |
| 2.4 | 99 | 49 | 25 | 17 | 12 |
| 2.6 | 106 | 53 | 27 | 17 | 13 |
| 2.8 | 122 | 61 | 30 | 21 | 15 |
| 3 | 137 | 68 | 34 | 23 | 17 |
| 3.2 | 152 | 76 | 38 | 25 | 19 |
| 3.4 | 167 | 84 | 42 | 29 | 21 |
| 3.6 | 190 | 95 | 48 | 31 | 24 |
| 3.8 | 205 | 103 | 51 | 34 | 26 |
| 4 | 228 | 114 | 57 | 38 | 29 |
| 4.2 | 243 | 122 | 61 | 40 | 30 |
| 4.4 | 266 | 133 | 67 | 45 | 33 |
| 4.6 | 289 | 144 | 72 | 48 | 36 |
| 4.8 | 319 | 160 | 80 | 53 | 40 |
| 5 | 342 | 171 | 86 | 57 | 43 |
| 5.2 | 372 | 186 | 93 | 63 | 47 |
| 5.4 | 403 | 201 | 101 | 67 | 50 |
| 5.6 | 441 | 220 | 110 | 74 | 55 |
| 5.8 | 479 | 239 | 120 | 80 | 60 |
| 6 | 517 | 258 | 129 | 86 | 64.6 |
| 6.2 | 562 | 281 | 141 | 93 | 70 |
| 6.4 | 608 | 304 | 152 | 102 | 76 |
| 6.6 | 659 | 330 | 165 | 110 | 83 |
| 6.8 | 722 | 361 | 181 | 117 | 90 |
| 7 | 783 | 391 | 196 | 131 | 98 |
| 7.2 | 851 | 426 | 213 | 143 | 106 |
| 7.4 | 935 | 467 | 234 | 156 | 117 |
| 7.6 | 1026 | 513 | 257 | 171 | 128 |
| 7.8 | 1125 | 562 | 281 | 189 | 141 |
| 8 | 1246 | 623 | 312 | 208 | 156 |
| 8.2 | 1376 | 688 | 344 | 229 | 172 |
| 8.4 | 1543 | 771 | 386 | 257 | 193 |
| 8.6 | 1725 | 863 | 431 | 286 | 216 |
| 8.8 | 1923 | 961 | 481 | 322 | 240 |
| 9 | 2143 | 1072 | 536 | 359 | 268 |

TABLE 6-continued

| Stick Chloride | Stick Creatinine | | | | |
|---|---|---|---|---|---|
| | 10 | 50 | 100 | 200 | 300 |
| 2000 mg 24-Hour Creatinine | | | | | |
| 2 | 80 | 40 | 20 | 13 | 10 |
| 2.2 | 88 | 44 | 22 | 14 | 11 |
| 2.4 | 104 | 52 | 26 | 18 | 13 |
| 2.6 | 112 | 56 | 28 | 18 | 14 |
| 2.8 | 128 | 64 | 32 | 22 | 16 |
| 3 | 144 | 72 | 36 | 24 | 18 |
| 3.2 | 160 | 80 | 40 | 26 | 20 |
| 3.4 | 176 | 88 | 44 | 30 | 22 |
| 3.6 | 200 | 100 | 50 | 33 | 25 |
| 3.8 | 216 | 108 | 54 | 36 | 27 |
| 4 | 240 | 120 | 60 | 40 | 30 |
| 4.2 | 256 | 128 | 64 | 42 | 32 |
| 4.4 | 280 | 140 | 70 | 47 | 35 |
| 4.6 | 304 | 152 | 76 | 50 | 38 |
| 4.8 | 336 | 168 | 84 | 56 | 42 |
| 5 | 360 | 180 | 90 | 60 | 45 |
| 5.2 | 392 | 196 | 98 | 66 | 49 |
| 5.4 | 424 | 212 | 106 | 70 | 53 |
| 5.6 | 464 | 232 | 116 | 78 | 58 |
| 5.8 | 504 | 252 | 126 | 84 | 63 |
| 6 | 544 | 272 | 136 | 90 | 68 |
| 6.2 | 592 | 296 | 148 | 98 | 74 |
| 6.4 | 640 | 320 | 160 | 107 | 80 |
| 6.6 | 694 | 347 | 174 | 116 | 87 |
| 6.8 | 760 | 380 | 190 | 123 | 95 |
| 7 | 824 | 412 | 206 | 138 | 103 |
| 7.2 | 896 | 448 | 224 | 150 | 112 |
| 7.4 | 984 | 492 | 246 | 164 | 123 |
| 7.6 | 1080 | 540 | 270 | 180 | 135 |
| 7.8 | 1184 | 592 | 296 | 199 | 148 |
| 8 | 1312 | 656 | 328 | 219 | 164 |
| 8.2 | 1448 | 724 | 362 | 241 | 181 |
| 8.4 | 1624 | 812 | 406 | 270 | 203 |
| 8.6 | 1816 | 908 | 454 | 301 | 227 |
| 8.8 | 2024 | 1012 | 506 | 339 | 253 |
| 9 | 2256 | 1128 | 564 | 378 | 282 |
| 2100 mg 24-Hour Creatinine | | | | | |
| 2 | 84 | 42 | 21 | 14 | 11 |
| 2.2 | 92 | 46 | 23 | 15 | 12 |
| 2.4 | 109 | 55 | 27 | 19 | 14 |
| 2.6 | 118 | 59 | 29 | 19 | 15 |
| 2.8 | 134 | 67 | 34 | 23 | 17 |
| 3 | 151 | 76 | 38 | 25 | 19 |
| 3.2 | 168 | 84 | 42 | 27 | 21 |
| 3.4 | 185 | 92 | 46 | 32 | 23 |
| 3.6 | 210 | 105 | 53 | 35 | 26 |
| 3.8 | 227 | 113 | 57 | 38 | 28 |
| 4 | 252 | 126 | 63 | 42 | 32 |
| 4.2 | 269 | 134 | 67 | 44 | 34 |
| 4.4 | 294 | 147 | 74 | 49 | 37 |
| 4.6 | 319 | 160 | 80 | 53 | 40 |
| 4.8 | 353 | 176 | 88 | 59 | 44 |
| 5 | 378 | 189 | 95 | 63 | 47 |
| 5.2 | 412 | 206 | 103 | 69 | 51 |
| 5.4 | 445 | 223 | 111 | 74 | 56 |
| 5.6 | 487 | 244 | 122 | 82 | 61 |
| 5.8 | 529 | 265 | 132 | 88 | 66 |
| 6 | 571 | 286 | 143 | 95 | 71 |
| 6.2 | 622 | 311 | 155 | 103 | 78 |
| 6.4 | 672 | 336 | 168 | 112 | 84 |
| 6.6 | 729 | 364 | 183 | 122 | 91 |
| 6.8 | 798 | 399 | 200 | 129 | 100 |
| 7 | 865 | 433 | 216 | 145 | 108 |
| 7.2 | 941 | 470 | 235 | 158 | 118 |
| 7.4 | 1033 | 517 | 258 | 172 | 129 |
| 7.6 | 1134 | 567 | 284 | 189 | 142 |
| 7.8 | 1243 | 622 | 311 | 209 | 155 |
| 8 | 1378 | 689 | 344 | 230 | 172 |
| 8.2 | 1520 | 760 | 380 | 253 | 190 |
| 8.4 | 1705 | 853 | 426 | 284 | 213 |
| 8.6 | 1907 | 953 | 477 | 316 | 238 |
| 8.8 | 2125 | 1063 | 531 | 356 | 266 |
| 9 | 2369 | 1184 | 592 | 397 | 296 |
| 2200 mg 24-Hour Creatinine | | | | | |
| 2 | 88 | 44 | 22 | 14 | 11 |
| 2.2 | 97 | 48 | 24 | 15 | 12 |
| 2.4 | 114 | 57 | 29 | 18 | 14 |
| 2.6 | 123 | 62 | 31 | 20 | 15 |
| 2.8 | 141 | 70 | 35 | 24 | 18 |
| 3 | 158 | 79 | 40 | 26 | 20 |
| 3.2 | 176 | 88 | 44 | 29 | 22 |
| 3.4 | 194 | 97 | 48 | 33 | 24 |
| 3.6 | 220 | 110 | 55 | 36 | 28 |
| 3.8 | 238 | 119 | 59 | 40 | 30 |
| 4 | 264 | 132 | 66 | 44 | 33 |
| 4.2 | 282 | 141 | 70 | 46 | 35 |
| 4.4 | 308 | 154 | 77 | 52 | 39 |
| 4.6 | 334 | 167 | 84 | 55 | 42 |
| 4.8 | 370 | 185 | 92 | 62 | 46 |
| 5 | 396 | 198 | 99 | 66 | 50 |
| 5.2 | 431 | 216 | 108 | 73 | 54 |
| 5.4 | 466 | 233 | 117 | 77 | 58 |
| 5.6 | 510 | 255 | 128 | 86 | 64 |
| 5.8 | 554 | 277 | 139 | 92 | 69 |
| 6 | 598 | 299 | 150 | 99 | 75 |
| 6.2 | 651 | 326 | 163 | 108 | 81 |
| 6.4 | 704 | 352 | 176 | 118 | 88 |
| 6.6 | 763 | 382 | 191 | 128 | 96 |
| 6.8 | 836 | 418 | 209 | 135 | 105 |
| 7 | 906 | 453 | 227 | 152 | 113 |
| 7.2 | 986 | 493 | 246 | 165 | 123 |
| 7.4 | 1082 | 541 | 271 | 180 | 135 |
| 7.6 | 1188 | 594 | 297 | 198 | 149 |
| 7.8 | 1302 | 651 | 326 | 219 | 163 |
| 8 | 1443 | 722 | 361 | 241 | 180 |
| 8.2 | 1593 | 796 | 398 | 265 | 199 |
| 8.4 | 1786 | 893 | 447 | 297 | 223 |
| 8.6 | 1998 | 999 | 499 | 331 | 250 |
| 8.8 | 2226 | 1113 | 557 | 373 | 278 |
| 9 | 2482 | 1241 | 620 | 416 | 310 |
| 2300 mg 24-Hour Creatinine | | | | | |
| 2 | 92 | 46 | 23 | 15 | 12 |
| 2.2 | 101 | 51 | 25 | 16 | 13 |
| 2.4 | 120 | 60 | 30 | 20 | 15 |
| 2.6 | 129 | 64 | 32 | 21 | 16 |
| 2.8 | 147 | 74 | 37 | 25 | 18 |
| 3 | 166 | 83 | 41 | 28 | 21 |
| 3.2 | 184 | 92 | 46 | 30 | 23 |
| 3.4 | 202 | 101 | 51 | 35 | 25 |
| 3.6 | 230 | 115 | 58 | 38 | 29 |
| 3.8 | 248 | 124 | 62 | 41 | 31 |
| 4 | 276 | 138 | 69 | 46 | 35 |
| 4.2 | 294 | 147 | 74 | 48 | 37 |
| 4.4 | 322 | 161 | 81 | 54 | 40 |
| 4.6 | 350 | 175 | 87 | 58 | 44 |
| 4.8 | 386 | 193 | 97 | 64 | 48 |
| 5 | 414 | 207 | 104 | 69 | 52 |
| 5.2 | 451 | 225 | 113 | 76 | 56 |
| 5.4 | 488 | 244 | 122 | 81 | 61 |
| 5.6 | 534 | 267 | 133 | 90 | 67 |
| 5.8 | 580 | 290 | 145 | 97 | 72 |
| 6 | 626 | 313 | 156 | 104 | 78 |
| 6.2 | 681 | 340 | 170 | 113 | 85 |
| 6.4 | 736 | 368 | 184 | 123 | 92 |
| 6.6 | 798 | 399 | 200 | 133 | 100 |
| 6.8 | 874 | 437 | 219 | 141 | 109 |
| 7 | 948 | 474 | 237 | 159 | 118 |
| 7.2 | 1030 | 515 | 258 | 173 | 129 |
| 7.4 | 1132 | 566 | 283 | 189 | 141 |
| 7.6 | 1242 | 621 | 311 | 207 | 155 |
| 7.8 | 1362 | 681 | 340 | 229 | 170 |
| 8 | 1509 | 754 | 377 | 252 | 189 |
| 8.2 | 1665 | 833 | 416 | 277 | 208 |
| 8.4 | 1868 | 934 | 467 | 311 | 233 |
| 8.6 | 2088 | 1044 | 522 | 346 | 261 |
| 8.8 | 2328 | 1164 | 582 | 390 | 291 |
| 9 | 2594 | 1297 | 649 | 434 | 324 |

TABLE 6-continued

| Stick Chloride | Stick Creatinine | | | | |
|---|---|---|---|---|---|
| | 10 | 50 | 100 | 200 | 300 |
| 2400 mg 24-Hour Creatinine | | | | | |
| 2 | 96 | 48 | 24 | 16 | 12 |
| 2.2 | 106 | 53 | 26 | 17 | 13 |
| 2.4 | 125 | 62 | 31 | 21 | 16 |
| 2.6 | 134 | 67 | 34 | 22 | 17 |
| 2.8 | 154 | 77 | 38 | 26 | 19 |
| 3 | 173 | 86 | 43 | 29 | 22 |
| 3.2 | 192 | 96 | 48 | 31 | 24 |
| 3.4 | 211 | 106 | 53 | 36 | 26 |
| 3.6 | 240 | 120 | 60 | 40 | 30 |
| 3.8 | 259 | 130 | 65 | 43 | 32 |
| 4 | 288 | 144 | 72 | 48 | 36 |
| 4.2 | 307 | 154 | 77 | 50 | 38 |
| 4.4 | 336 | 168 | 84 | 56 | 42 |
| 4.6 | 365 | 182 | 92 | 60 | 46 |
| 4.8 | 403 | 202 | 101 | 67 | 50 |
| 5 | 432 | 216 | 108 | 72 | 54 |
| 5.2 | 470 | 235 | 118 | 79 | 59 |
| 5.4 | 509 | 254 | 127 | 84 | 64 |
| 5.6 | 557 | 278 | 139 | 94 | 70 |
| 5.8 | 605 | 302 | 151 | 101 | 76 |
| 6 | 653 | 326 | 163 | 108 | 82 |
| 6.2 | 710 | 355 | 178 | 118 | 89 |
| 6.4 | 768 | 384 | 192 | 128 | 96 |
| 6.6 | 833 | 416 | 209 | 139 | 104 |
| 6.8 | 912 | 456 | 228 | 148 | 114 |
| 7 | 989 | 494 | 247 | 166 | 124 |
| 7.2 | 1075 | 538 | 269 | 180 | 134 |
| 7.4 | 1181 | 590 | 296 | 197 | 148 |
| 7.6 | 1296 | 648 | 324 | 216 | 162 |
| 7.8 | 1421 | 710 | 355 | 239 | 178 |
| 8 | 1574 | 787 | 394 | 263 | 197 |
| 8.2 | 1738 | 869 | 434 | 289 | 217 |
| 8.4 | 1949 | 974 | 487 | 324 | 244 |
| 8.6 | 2179 | 1090 | 545 | 361 | 272 |
| 8.8 | 2429 | 1214 | 607 | 407 | 304 |
| 9 | 2707 | 1354 | 677 | 454 | 338 |
| 2500 mg 24-Hour Creatinine | | | | | |
| 2 | 100 | 50 | 25 | 16 | 13 |
| 2.2 | 110 | 55 | 28 | 18 | 14 |
| 2.4 | 130 | 65 | 33 | 23 | 16 |
| 2.6 | 140 | 70 | 35 | 23 | 18 |
| 2.8 | 160 | 80 | 40 | 28 | 20 |
| 3 | 180 | 90 | 45 | 30 | 23 |
| 3.2 | 200 | 100 | 50 | 33 | 25 |
| 3.4 | 220 | 110 | 55 | 38 | 28 |
| 3.6 | 250 | 125 | 63 | 41 | 31 |
| 3.8 | 270 | 135 | 68 | 45 | 34 |
| 4 | 300 | 150 | 75 | 50 | 38 |
| 4.2 | 320 | 160 | 80 | 53 | 40 |
| 4.4 | 350 | 175 | 88 | 59 | 44 |
| 4.6 | 380 | 190 | 95 | 63 | 48 |
| 4.8 | 420 | 210 | 105 | 70 | 53 |
| 5 | 450 | 225 | 113 | 75 | 56 |
| 5.2 | 490 | 245 | 123 | 83 | 61 |
| 5.4 | 530 | 265 | 133 | 88 | 66 |
| 5.6 | 580 | 290 | 145 | 98 | 73 |
| 5.8 | 630 | 315 | 158 | 105 | 79 |
| 6 | 680 | 340 | 170 | 113 | 85 |
| 6.2 | 740 | 370 | 185 | 123 | 93 |
| 6.4 | 800 | 400 | 200 | 134 | 100 |
| 6.6 | 868 | 434 | 218 | 145 | 109 |
| 6.8 | 950 | 475 | 238 | 154 | 119 |
| 7 | 1030 | 515 | 258 | 173 | 129 |
| 7.2 | 1120 | 560 | 280 | 188 | 140 |
| 7.4 | 1230 | 615 | 308 | 205 | 154 |
| 7.6 | 1350 | 675 | 338 | 225 | 169 |
| 7.8 | 1480 | 740 | 370 | 249 | 185 |
| 8 | 1640 | 820 | 410 | 274 | 205 |
| 8.2 | 1810 | 905 | 453 | 301 | 226 |
| 8.4 | 2030 | 1015 | 508 | 338 | 254 |
| 8.6 | 2270 | 1135 | 568 | 377 | 284 |
| 8.8 | 2530 | 1265 | 633 | 424 | 316 |
| 9 | 2820 | 1410 | 705 | 473 | 353 |
| 2600 mg 24-Hour Creatinine | | | | | |
| 2 | 104 | 52 | 26 | 17 | 13 |
| 2.2 | 114 | 57 | 29 | 18 | 14 |
| 2.4 | 135 | 68 | 34 | 23 | 17 |
| 2.6 | 146 | 73 | 36 | 23 | 18 |
| 2.8 | 166 | 83 | 42 | 29 | 21 |
| 3 | 187 | 94 | 47 | 31 | 23 |
| 3.2 | 208 | 104 | 52 | 34 | 26 |
| 3.4 | 229 | 114 | 57 | 39 | 29 |
| 3.6 | 260 | 130 | 65 | 43 | 33 |
| 3.8 | 281 | 140 | 70 | 47 | 35 |
| 4 | 312 | 156 | 78 | 52 | 39 |
| 4.2 | 333 | 166 | 83 | 55 | 42 |
| 4.4 | 364 | 182 | 91 | 61 | 46 |
| 4.6 | 395 | 198 | 99 | 65 | 49 |
| 4.8 | 437 | 218 | 109 | 73 | 55 |
| 5 | 468 | 234 | 117 | 78 | 59 |
| 5.2 | 510 | 255 | 127 | 86 | 64 |
| 5.4 | 551 | 276 | 138 | 91 | 69 |
| 5.6 | 603 | 302 | 151 | 101 | 75 |
| 5.8 | 655 | 328 | 164 | 109 | 82 |
| 6 | 707 | 354 | 177 | 117 | 88 |
| 6.2 | 770 | 385 | 192 | 127 | 96 |
| 6.4 | 832 | 416 | 208 | 139 | 104 |
| 6.6 | 902 | 451 | 226 | 151 | 113 |
| 6.8 | 988 | 494 | 247 | 160 | 124 |
| 7 | 1071 | 536 | 268 | 179 | 134 |
| 7.2 | 1165 | 582 | 291 | 195 | 146 |
| 7.4 | 1279 | 640 | 320 | 213 | 160 |
| 7.6 | 1404 | 702 | 351 | 234 | 176 |
| 7.8 | 1539 | 770 | 385 | 259 | 192 |
| 8 | 1706 | 853 | 426 | 285 | 213 |
| 8.2 | 1882 | 941 | 471 | 313 | 235 |
| 8.4 | 2111 | 1056 | 528 | 351 | 264 |
| 8.6 | 2361 | 1180 | 590 | 391 | 295 |
| 8.8 | 2631 | 1316 | 656 | 441 | 329 |
| 9 | 2933 | 1466 | 733 | 491 | 367 |
| 2700 mg 24-Hour Creatinine | | | | | |
| 2 | 108 | 54 | 27 | 18 | 14 |
| 2.2 | 119 | 59 | 30 | 19 | 15 |
| 2.4 | 140 | 70 | 35 | 24 | 18 |
| 2.6 | 151 | 76 | 38 | 24 | 19 |
| 2.8 | 173 | 86 | 43 | 30 | 22 |
| 3 | 194 | 97 | 49 | 32 | 24 |
| 3.2 | 216 | 108 | 54 | 35 | 27 |
| 3.4 | 238 | 119 | 59 | 41 | 30 |
| 3.6 | 270 | 135 | 68 | 45 | 34 |
| 3.8 | 292 | 146 | 73 | 49 | 36 |
| 4 | 324 | 162 | 81 | 54 | 41 |
| 4.2 | 346 | 173 | 86 | 57 | 43 |
| 4.4 | 378 | 189 | 95 | 63 | 47 |
| 4.6 | 410 | 205 | 103 | 68 | 51 |
| 4.8 | 454 | 227 | 113 | 76 | 57 |
| 5 | 486 | 243 | 122 | 81 | 61 |
| 5.2 | 529 | 265 | 132 | 89 | 66 |
| 5.4 | 572 | 286 | 143 | 95 | 72 |
| 5.6 | 626 | 313 | 157 | 105 | 78 |
| 5.8 | 680 | 340 | 170 | 113 | 85 |
| 6 | 734 | 367 | 184 | 122 | 92 |
| 6.2 | 799 | 400 | 200 | 132 | 100 |
| 6.4 | 864 | 432 | 216 | 144 | 108 |
| 6.6 | 937 | 468 | 235 | 157 | 117 |
| 6.8 | 1026 | 513 | 257 | 166 | 128 |
| 7 | 1112 | 556 | 278 | 186 | 139 |
| 7.2 | 1210 | 605 | 302 | 203 | 151 |
| 7.4 | 1328 | 664 | 332 | 221 | 166 |
| 7.6 | 1458 | 729 | 365 | 243 | 182 |
| 7.8 | 1598 | 799 | 400 | 269 | 200 |
| 8 | 1771 | 886 | 443 | 296 | 221 |
| 8.2 | 1955 | 977 | 489 | 325 | 244 |
| 8.4 | 2192 | 1096 | 548 | 365 | 274 |

TABLE 6-continued

| Stick Chloride | Stick Creatinine | | | | |
|---|---|---|---|---|---|
| | 10 | 50 | 100 | 200 | 300 |
| 8.6 | 2452 | 1226 | 613 | 406 | 306 |
| 8.8 | 2732 | 1366 | 683 | 458 | 342 |
| 9 | 3046 | 1523 | 761 | 510 | 381 |

Example 3

Correlations

1. The correlation between urine chloride excretion and urine sodium excretion in 24-hour urine collections for 88 collections was r=0.97. Measurements of chloride and sodium were performed by generally accepted clinical laboratory methods.
2. The correlation between urine chloride concentration determined by dipstick and by a generally accepted clinical laboratory method for 46 samples was r=0.78. In 41 comparisons made independently by each of two observers, the correlation as read by observer #1 was r=0.85 and by observer #2 was r=0.75. The inter-observer agreement was r=0.85.
3. The correlation between urine creatinine concentrations determined by dipstick and by a generally accepted clinical laboratory method in 47 samples was r=0.81. In 41 comparisons made independently by each of two observers, the correlation as read by observer #1 was r=0.75 and by observer #2 was r=0.75. The inter-observer agreement was r=0.88.
4. The correlation between the chloride/creatinine ratio obtained by dipsticks versus that measured by accepted clinical laboratory methods was: r=0.82; n=46.
5. The correlation between dipstick and laboratory chloride/creatinine ratios was: r=0.68; n=46.
6. The spot urine chloride/creatinine ratio, by itself, without adjustment for 24-hour creatinine excretion did not correlate well with directly measured 24-hour chloride excretion or with directly measured sodium excretion, r=−0.12 (n=34) for dipsticks, and r=−0.10, (n=36) using laboratory measurements
7. The correlation between chloride/creatinine ratios that were adjusted for 24-hour creatinine excretion, and actual 24-hour sodium excretion measurements, was examined in spot samples collected at random times, in spot samples collected in the morning (second voided urine after awakening), and spot samples collected in the late afternoon/early evening before the evening meal. The time when the urine sample was collected did impact the accuracy of the chloride/creatinine ratios that were adjusted for 24-hour creatinine excretion. In particular, the adjusted chloride/creatinine ratio from spot urines collected at random times correlated poorly with actual 24-hour sodium excretion (r=0.12 for dipstick, 0.08 for laboratory, n=34). For the morning samples (n=37), correlations improved somewhat (r=0.41 for dipstick, and 0.27, for laboratory). However, the correlation between estimated and actually determined sodium excretion values improved markedly for samples collected in the late afternoon. Specifically, the highest correlation between estimated and actually measured sodium excretion values was when the subject took the spot urine sample immediately before the evening meal. At that time, the chloride/creatinine ratio determined by dipsticks (48 samples) and by laboratory measurements (47 samples), adjusted for 24-hour creatinine excretion according to the practice prescribed in Example 2, correlated strongly with directly measured 24-hour sodium excretion (r=0.71 and 0.79, respectively).
8. In the above observations, dipstick concentrations were measured independently by two observers. Inter-observer agreement was strong regarding predicted sodium excretion (r=0.86).
9. The following equation is used to derive the 24-hour sodium-excretion of a subject from measured chloride and creatinine concentrations, adjusted for 24-hour creatinine excretion (using Table 1), wherein [chloride] is chloride concentration, [creatinine] is creatinine concentration:

$$\frac{\text{sample [chloride] } (mEq/L) \times \text{24-hr urine creatinine excretion} (mg)}{\text{sample [creatinine] } (mg/dL) \times 10} = \text{24-hr chloride excretion } (mEq)$$

For example, if chloride concentration is 50 mEq/L, creatinine concentration is 100 mg/dL, and 24-hr urine creatinine excretion is 2000 mg, then $$\frac{50}{100 \times 10} \times 2000 = 100 \; mEq/\text{day}.$$

This, the 24-hour chloride excretion for the individual with a spot urine chloride concentration of 50 mEq/L, a spot creatinine concentration of 100 mg/dL, and a 24-hr urine creatinine excretion of 2000 mg, is 100 mEq/day.

To further establish that the semi-quantitative determination of sodium excretion described in Example 2 comports with the actual 24-hour excretion of sodium determined by the method prescribed in Example 3, subjects were classified by their directly measured 24-hour chloride and sodium excretion and the 24-hour sodium excretion predicted by the semi-quantitative means prescribed in Example 2. Agreement between the two was evaluated, as shown in Tables 7-10.

TABLE 7

Relationship between predicted 24-hour chloride excretion using AM-collected spot urine samples, and actual 24-hour chloride excretion

| | Actual | | |
|---|---|---|---|
| Predicted | Low (<100 mEq/day) | Medium (100-200 mEq/day) | High (>200 mEq/day) |
| Low | 5 | 5 | 2 |
| Medium | 3 | 11 | 2 |
| High | | 4 | 5 |

TABLE 8

Relationship between predicted 24-hour chloride excretion using PM-collected spot urine samples, and actual 24-hour chloride excretion

| | Actual | | |
|---|---|---|---|
| Predicted | Low (<100 mEq/day) | Medium (100-200 mEq/day) | High (>200 mEq/day) |
| Low | 12 | 3 | 2 |
| Medium | 1 | 18 | 1 |
| High | | 4 | 7 |

TABLE 9

Relationship between predicted 24-hour chloride excretion using AM-collected spot urine samples, and actual 24-hour sodium excretion

| | Actual | | |
|---|---|---|---|
| Predicted | Low (<100 mEq/day) | Medium (100-200 mEq/day) | High (>200 mEq/day) |
| Low | 5 | 5 | 2 |
| Medium | 4 | 10 | 2 |
| High | | 4 | 5 |

TABLE 10

Relationship between predicted 24-hour chloride excretion using PM-collected spot urine sample and actual 24-hour sodium excretion

| | Actual | | |
|---|---|---|---|
| Predicted | Low (<100 mEq/day) | Medium (100-200 mEq/day) | High (>200 mEq/day) |
| Low | 11 | 4 | 2 |
| Medium | 2 | 16 | 2 |
| High | | 5 | 6 |

Example 4

24-hour Urine Collections

To validate embodiments of the invention, formulae were generated to estimate "normalized" 24-hour creatinine excretion values from different populations of people using data obtained directly from actual 24-hour collections of urine. This Example describes how 24 hour collections of urine were taken and analyzed for creatinine. Such determinations were used to generate the normalized 24 hour creatinine values listed in Table 1. Similar methods can be used to determine normalized 24 hour creatinine values for other populations of subjects, e.g., subjects with of different ages, races, lean body masses, muscle masses, adiposities, physical activities, etc., or any combination thereof.

To maximize the accuracy of data obtained from 24-hour urine collections, steps were taken to guard against under-collection. In a previous study (J. Rheum. 31:1557, 2004) in which any collection greater than about 80% of expected total urine output was considered a "complete" collection, about 30% of collections were found to actually be incomplete. To guard against this problem, 24-hour creatinine excretion values that were below 1300 mg/day in males or below 600 mg/day in females were regarded to be from incomplete collections and were not included in deriving regression formulae used to populate the cells of look-up tables, e.g., those in Table 1). Where such formulae are refined with a larger number of subjects, any 24-hour creatinine excretion value that is <20 mg/kg in males or <15 mg/kg in females is rejected as being an incomplete collection, as previously described (BMJ 287:929, 1983).

The need for criteria to determine what is a complete 24-hour collection of urine is illustrated by the following Table 11. As seen in Table 11, based on actual creatinine values in 24 hour urine collections, incomplete collection yields lower urine sodium determination than is observed when the collection is complete. There was no reason to believe that subjects with such incomplete collections consume less salt than those with complete collections. Calculating a subject's 24 hour excretion of sodium using the 24 hour normalized creatinine values described herein brings the subject's calculated 24-hour sodium excretion levels up to the same level as observed for subjected with complete 24-hour urine collections.

TABLE 11

| | Complete Collectors (N = 29) | Incomplete Collectors (N = 26) |
|---|---|---|
| Creatinine measures | | |
| Mean 24-hr urinary creatinine excretion | 1670 | 1115 |
| Mean estimated 24-hr urinary creatinine | 1670 | 1639 |
| Sodium measures | | |
| Mean 24-hr urinary sodium excretion | 170 | 135 |
| Mean predicted sodium excretion (dipstick measurement using actual 24-hour creatinine excretion values - from 24-hr urine collections | 184 | 129 |
| Mean predicted sodium excretion (dipstick measurement using normalized 24-hr creatinine values obtained from table) | 185 | 199 |

Example 5

Creation of the Nomograms

Step 1: Nomogram for estimated 24-hour urine creatinine excretion. Based on the 24-hour urine data obtained, an equation can be developed that estimates 24-hour creatinine excretion from variables such as gender, race, age, weight, lean muscle mass and adiposity. The user, without doing any actual calculations, simply goes to Table 1 or Table 11, identifies the characteristics applicable to the subject (e.g., race, gender, weight and/or age) and easily locates the subject's normalized 24-hour urine creatinine excretion.

Multivariate regression analyses were performed to derive an equation for calculation of the estimated 24-hour urinary creatinine excretion The r square for the multivariate model was 0.72 ($r=0.85$); the strongest predictors in the model were weight ($p<0.001$) and gender ($p=0.004$). Therefore, the derived equation, based on data from actual 24-hour urine collections, incorporates variables including race, gender and weight.

Preliminary findings from a sample of 29 individuals yielded a strong model of normalized 24-hour urinary creatinine excretion, yielding the following equation:

$$y = 1150 - 407.4 \text{ if female} + 5.7 \times \text{weight} - 88 \text{ if white} \quad \text{I}$$

Inclusion of additional data from additional individuals yielded another strong model for normalized 24-hour urinary creatinine excretion:

$$y = 654 \text{ mg} - 537.3 \text{ mg(if female)} + (7.3)(\text{weight in pounds}) - 59.3 \text{ mg(if white)} \quad \text{II}$$

In the subject population, age was not a significant variable. However, age could be included in such an equation after inclusion of data from more subjects in further studies.

When formula II was applied to a new test population it provided an estimate of sodium excretion that correlated very strongly with the actual sodium excretion in people who provided a complete 24 hour collection.

The accuracy of the formula-derived estimates of 24-hour urine creatinine, can be further confirmed by comparing the correlation of the estimated versus actual 24-hour urine creatinine with actual measurements of the amount of creatinine in 24 hour urine samples, or by taking into account the lean muscle mass of subjects, as determined by a Tanita body composition monitor. The correlation between estimated 24-hour creatinine excretion and lean muscle mass was extremely strong, at $r=0.90$ (n=38). By comparison, the correlation between actual 24-hour creatinine excretion and lean muscle mass was $r=0.70$ (n=44). These observations support the validity of the normalized creatinine excretion values listed in Tables 1 and 12. It also indicates that in this example, the estimated creatinine excretion might even be superior to the actual measured creatinine excretion, because of the widespread problem of undercollection of 24 hour samples of urine as well as day-to-day variation due to changes in diet that affect actual measurements.

The cells of one column of Table 12 are populated for illustrative purposes to provide a nomogram for use by a subject of 50-59 years of age. Thus, for example, a 50 year-old white male who weighs 165 lbs would have an estimated 24-hour urine creatinine excretion of 1917 mg.

TABLE 12

Normalized Creatinine Excretion (mg) during 24 Hours for White Males

| Weight | Age | | | | |
|---|---|---|---|---|---|
| | 40-49 | 50-59 | 60-69 | 70-79 | 80-89 |
| 110-129 | | 1689 | | | |
| 130-149 | | 1803 | | | |
| 150-169 | | 1917 | | | |
| 170-189 | | 2031 | | | |
| 190-209 | | 2145 | | | |
| 210-229 | | 2259 | | | |
| 230-249 | | 2373 | | | |

Step 2. Nomogram for estimated 24-hour urine sodium excretion. After identifying normalized 24-hour urine creatinine excretion values as described above (e.g., those in Table 1 or 12), the user selects a page from Table 6 that recites the value closest to the normalized 24-hour creatinine excretion value for the subject. As shown, the pages of Table 6, incrementally recite normalized 24 hour creatinine excretion values of that increase by 100 mg/day (e.g., 1000, 1100, 1200, . . . 2700 mg/day).

Using the table on the page corresponding to his/her normalized 24-hour creatinine excretion value, the user identifies his/her estimated 24-hour sodium excretion by simply locating the column with the creatinine concentration measured in his/her urine sample, and the row with the chloride concentration measured in the sample. These tables are constructed from simple mathematical formulae, using the following equation.

$$\frac{\text{sample [chloride]} \times \text{normalized creatinine value}}{\text{sample [creatinine]}} \approx \text{subject's 24-hr sodium excretion}$$

One example of a table for identifying the 24 hour excretion of sodium by a subject is Table 6.

In view of the above, it will be seen that the several objects of the invention are achieved and other advantageous results attained.

As various changes could be made in the above kits, nomograms and methods without departing from the scope of the invention, it is intended that all matter contained in the above description and shown in the accompanying drawings shall be interpreted as illustrative and not in a limiting sense.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. The terms "comprising", "including" and "having" are intended to be inclusive and mean that there may be additional elements other than the listed elements.

As used herein and in the appended claims, the singular forms "a," "an," and "the" include plural reference unless the context clearly dictates otherwise. Thus, for example, a reference to "an antibody" includes a plurality (for example, a solution of antibodies or a series of antibody preparations) of such antibodies, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed:

1. A method of determining a subject's 24-hour urinary excretion of an analyte from a single sample of the subject's urine, comprising:
    measuring the analyte concentration in the single urine sample;
    measuring creatinine concentration in the single urine sample;
    using the subject's age, gender, race, weight, muscle mass, lean body mass, muscle mass, adiposity, physical activity, or a combination thereof, to select a normalized 24-hour creatinine excretion value from an array of normalized 24-hour creatinine excretion values, wherein each normalized 24-hour creatinine excretion value is an estimated mean of observed 24-hour urine creatinine concentrations for a population of persons of similar age, gender, race, weight, muscle mass, lean body mass, muscle mass, adiposity, and/or physical activity; and
    using the normalized 24-hour creatinine excretion value, the measured analyte concentration, and the measured creatinine concentration to determine the 24-hour urinary excretion of analyte for the subject.

2. The method of claim 1, wherein the analyte is chloride, albumin, catecholamine, calcium, methylmalonic acid, zinc, magnesium, n-terminal telopeptide (NTx) or a combination thereof.

3. The method of claim 1, wherein the 24-hour urinary excretion of analyte for the subject is determined by identifying the subject's 24-hour analyte excretion from an array of 24-hour urinary analyte excretion values that vary depending upon values for normalized 24-hour creatinine excretion, analyte concentration, and creatinine concentration.

4. The method of claim 1, wherein the 24-hour urinary excretion of the analyte for the subject is determined using the following formula:

$$\frac{\text{sample} \times \text{normalized 24 hr creatinine value}}{\text{sample}} = \text{subject's 24-hr analyte excretion}$$

wherein:
    sample is the measured concentration of analyte in the subject's single urine sample;
    sample is the measured concentration of creatinine in the subject's single urine sample;
    normalized 24 hr creatinine value is the normalized 24-hour creatinine excretion value; and
    subject's 24-hour analyte excretion is the determined amount of analyte excreted by the subject over 24 hours.

5. The method of claim 1, wherein the subject's gender, race and weight are used to select the normalized 24-hour creatinine excretion value from the array of normalized 24-hour creatinine excretion values.

6. The method of claim 1, wherein each normalized 24-hour creatinine excretion value is an estimated mean (from regression analysis) of observed 24-hour urine creatinine concentrations for a population of persons of similar gender, race, and weight.

7. The method of claim 1, wherein the single urine sample is obtained approximately half-way through the subject's waking cycle, and several hours after a significant meal.

8. The method of claim 1, wherein the single urine sample is obtained in late afternoon or early evening, before the evening meal.

9. The method of claim 1, wherein the single urine sample is obtained by the subject at home or work, the concentrations are measured by the subject at home and the subject's 24-hour urinary analyte excretion is determined by the subject at home or work.

10. The method of claim 1, wherein the single urine sample is obtained by the subject, the concentrations are measured by a health care professional and the subject's 24-hour urinary analyte excretion is determined by a health care professional.

11. The method of claim 1, wherein measurement of the analyte concentration and/or the creatinine concentration is quantitative.

12. The method of claim 1, wherein measurement of the analyte concentration and/or the creatinine concentration is semi-quantitative.

13. The method of claim 1, wherein measurement of the analyte concentration and/or the creatinine concentration yields a numerical value or a range of numerical values.

14. The method of claim 1, wherein the determined 24-hour urinary excretion of analyte for the subject is a numerical value or a range of numerical values.

15. The method of claim 1, wherein the determined 24-hour urinary excretion of analyte for the subject is an indication that the 24-hour urinary excretion of analyte for the subject is low, medium or high.

16. The method of claim 1, wherein the analyte concentration is measured using amperometry, fluorimetry, spectrometry, nuclear magnetic resonance, atomic emission spectrometry, atomic absorption spectrometry, gravimetry, titrimetry, colorimetry, enzyme linked immunosorbant assay (ELISA), high pressure liquid chromatography (HPLC), spectrometry, colorimetry, gas chromatography, mass spectrometry, enzymatic assay, electrophoretically or a combination thereof.

17. The method of claim 1, wherein the analyte concentration and/or the creatinine concentration are measured without the use of a laboratory instrument.

18. The method of claim 1, wherein the analyte concentration and/or the creatinine concentration in the subject's urine are measured using a dipstick.

19. The method of claim 18, wherein measurement of the analyte concentration and/or the creatinine concentration with a dipstick yields a numerical value.

20. The method of claim 18, wherein measurement of the analyte concentration and/or the creatinine concentration with a dipstick yields a colorimetric readout.

21. The method of claim 1, wherein the array of normalized 24-hour creatinine excretion values is calculated using either of the following formulae:

$$y=1150\text{mg}-407.4\text{mg}(\text{if female})+(5.7)(\text{weight in pounds})-88\text{mg}(\text{if white}) \qquad \text{I}$$

$$y=654\text{mg}-537.3\text{mg}(\text{if female})+(7.3)(\text{weight in pounds})-59.3\text{mg}(\text{if white}) \qquad \text{II}$$

wherein y is a normalized 24-hr creatinine excretion value in milligrams.

22. A method of determining a subject's 24-hour urinary excretion of sodium from a single sample of the subject's urine, comprising:
measuring chloride concentration in the single urine sample;
measuring creatinine concentration in the single urine sample;
using the subject's age, gender, race, weight, muscle mass, lean body mass, muscle mass, adiposity, physical activity, or a combination thereof, to select a normalized 24-hour creatinine excretion value from an array of normalized 24-hour creatinine excretion values, wherein each normalized 24-hour creatinine excretion value is an estimated mean of observed 24-hour urine creatinine concentrations for a population of persons of similar age, gender, race, weight, muscle mass, lean body mass, muscle mass, adiposity, and/or physical activity; and
using the normalized 24-hour creatinine excretion value, the measured chloride concentration, and the measured creatinine concentration to determine the 24-hour urinary excretion of sodium for the subject.

23. The method of claim 22, wherein the 24-hour urinary excretion of sodium for the subject is determined by identifying the subject's 24-hour sodium excretion from an array of 24-hour urinary sodium excretion values that vary depending upon values for normalized 24-hour creatinine excretion, chloride concentration, and creatinine concentration.

24. The method of claim 22, wherein the 24-hour urinary excretion of sodium for the subject is determined using the following formula:

$$\frac{\text{sample} \times \text{normalized 24 hr creatinine value}}{\text{sample}} = \text{subject's 24-hr chloride excretion}$$

wherein:
sample is the measured concentration of chloride in the subject's single urine sample;
sample is the measured concentration of creatinine in the subject's single urine sample;
normalized creatinine value is the normalized 24-hour creatinine excretion value; and
determining the subject's 24-hour sodium excretion from the subject's 24-hr chloride excretion.

25. The method of claim 22, wherein the subject's gender, race and weight are used to select the normalized 24-hour creatinine excretion value from the array of normalized 24-hour creatinine excretion values.

26. The method of claim 22, wherein each normalized 24-hour creatinine excretion value is an estimated mean (from regression analysis) of observed 24-hour urine creatinine concentrations for a population of persons of similar gender, race, and weight.

27. The method of claim 22, wherein the single urine sample is obtained approximately half-way through the subject's waking cycle, and several hours after a significant meal.

28. The method of claim 22, wherein the single urine sample is obtained in late afternoon or early evening, before the evening meal.

29. The method of claim 22, wherein the single urine sample is obtained by the subject at home or work, the concentrations are measured by the subject at home and the subject's 24-hour urinary sodium excretion is determined by the subject at home or work.

30. The method of claim 22, wherein the single urine sample is obtained by the subject, the concentrations are measured by a health care professional and the subject's 24-hour urinary sodium excretion is determined by a health care professional.

31. The method of claim 22, wherein measurement of the chloride concentration and/or the creatinine concentration is quantitative.

32. The method of claim 22, wherein measurement of the chloride concentration and/or the creatinine concentration is semi-quantitative.

33. The method of claim 22, wherein measurement of the chloride concentration and/or the creatinine concentration yields a numerical value or a range of numerical values.

34. The method of claim 22, wherein the determined 24-hour urinary excretion of sodium for the subject is a numerical value or a range of numerical values.

35. The method of claim 22, wherein the determined 24-hour urinary excretion of sodium for the subject is an indication that the 24-hour urinary excretion of sodium for the subject is low, medium or high.

36. The method of claim 22, wherein the chloride concentration is measured using amperometry, fluorimetry, spectrometry, nuclear magnetic resonance, atomic emission spectrometry, atomic absorption spectrometry, gravimetry, titrimetry, colorimetry, or a combination thereof.

37. The method of claim 22, wherein the creatinine concentration is measured using enzyme linked immunosorbant assay (ELISA), high pressure liquid chromatography (HPLC), spectrometry, colorimetry, gas chromatography, mass spectrometry, enzymatic assay, electrophoretically or a combination thereof.

38. The method of claim 22, wherein the chloride concentration and/or the creatinine concentration are measured without the use of a laboratory instrument.

39. The method of claim 22, wherein the chloride concentration and/or the creatinine concentration in the subject's urine are measured using a dipstick.

40. The method of claim 39, wherein measurement of the chloride concentration and/or the creatinine concentration with a dipstick yields a numerical value.

41. The method of claim 39, wherein measurement of the chloride concentration and/or the creatinine concentration with a dipstick yields a colorimetric readout.

42. The method of claim 22, wherein the array of normalized 24-hour creatinine excretion values is calculated using either of the following formulae:

$$y=1150\text{mg}-407.4\text{mg}(\text{if female})+(5.7)(\text{weight in pounds})-88\text{mg}(\text{if white}) \qquad \text{I}$$

$$y=654\text{mg}-537.3\text{mg}(\text{if female})+(7.3)(\text{weight in pounds})-59.3\text{mg}(\text{if white}) \qquad \text{II}$$

wherein y is a normalized 24-hr creatinine excretion value in milligrams.

43. A method of improving the accuracy of determining 24-hour urinary excretion of sodium by a subject from a single urine sample, comprising:
   measuring creatinine concentration and chloride concentration in a single urine sample obtained from a subject in late afternoon before consuming a meal;
   using the subject's gender, race and weight to select a normalized 24-hour creatinine excretion value from an array of normalized 24-hour creatinine excretion values, wherein each normalized 24-hour creatinine excretion value in the array is an estimated mean of observed 24-hour urine creatinine concentrations for a population of persons with the subject's gender, race and weight; and
   determining the subject's 24-hour urinary excretion of sodium.

44. The method of claim 43, wherein the 24-hour urinary excretion of sodium for the subject is determined using the following formula:

$$\frac{\text{sample} \times \text{normalized 24-hr creatinine value}}{\text{sample}} = \text{subject's 24-hr chloride excretion}$$

wherein:
   sample is the measured concentration of chloride in the subject's single urine sample;
   sample is the measured concentration of creatinine in the subject's single urine sample;
   normalized creatinine value is the normalized 24-hour creatinine excretion value; and
   determining the subject's 24-hour sodium excretion from the subject's 24 hour chloride excretion.

45. The method of claim 43, wherein the 24-hour urinary excretion of sodium for the subject is selected from an array of normalized 24-hour urinary sodium excretion values.

46. A kit for calculating 24-hour excretion of an analyte by a subject, the kit comprising:
   (a) a container for holding a single urine sample;
   (b) a device for measuring the analyte concentration in the single urine sample;
   (c) a device for measuring creatinine concentration in the single urine sample; and
   (d) instructions comprising a first nomogram listing normalized 24-hour creatinine excretion values for distinct populations of subjects, where the normalized 24-hour creatinine excretion values vary depending upon the populations' age, gender, race, weight, lean body mass, muscle mass, adiposity, physical activity, or a combination thereof, and a second nomogram listing calculated 24-hour analyte excretion values, where the calculated 24-hour analyte excretion values are derived from the normalized 24-hour urine creatinine excretion value for the subject, the analyte concentration in the spot urine sample and the creatinine concentration in the single urine sample.

47. The kit of claim 46, wherein the analyte is chloride, albumin, catecholamine, calcium, methylmalonic acid, zinc, magnesium, n-terminal telopeptide (NTx) or a combination thereof.

48. The kit of claim 46, wherein the analyte is chloride.

49. The kit of claim 48, wherein the calculated 24-hour analyte excretion values are calculated 24-hour sodium excretion values, and the analyte concentration is a chloride concentration in the single urine sample.

50. The kit of claim 46, wherein the devices are titrator dipsticks for colorimetric determination of the concentrations of the analyte and creatinine in the urine sample.

51. The kit of claim 46, wherein the first nomogram is an array or listing of normalized 24-hour creatinine excretion values that vary depending upon the populations' gender, race, and weight.

* * * * *